(12) United States Patent
Hryhorenko et al.

(10) Patent No.: US 11,104,742 B2
(45) Date of Patent: *Aug. 31, 2021

(54) ANTIBODIES TO QUETIAPINE AND USE THEREOF

(71) Applicant: JANSSEN PHARMACEUTICA NV, Beerse (BE)

(72) Inventors: Eric Hryhorenko, Hilton, NY (US); Banumathi Sankaran, Lexington, MA (US); Thomas R. DeCory, Pittsford, NY (US); Theresa Tubbs, Rochester, NY (US); Linda Colt, Rochester, NY (US); Bart M. Remmerie, Ghent (BE); Rhys Salter, Doylestown, PA (US); Matthew G. Donahue, Hattiesburg, MS (US); Yong Gong, Warrington, PA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 156 days.

This patent is subject to a terminal disclaimer.

(21) Appl. No.: 16/573,367

(22) Filed: Sep. 17, 2019

(65) Prior Publication Data

US 2020/0002438 A1    Jan. 2, 2020

Related U.S. Application Data

(63) Continuation of application No. 15/380,729, filed on Dec. 15, 2016, now Pat. No. 10,435,478.

(Continued)

(51) Int. Cl.
*C07K 16/44* (2006.01)
*G01N 33/94* (2006.01)

(52) U.S. Cl.
CPC ......... *C07K 16/44* (2013.01); *G01N 33/9406* (2013.01); *G01N 33/9466* (2013.01)

(58) Field of Classification Search
CPC . G01N 33/9466; G01N 33/9406; C07K 16/44
See application file for complete search history.

(56) References Cited

U.S. PATENT DOCUMENTS

| 4,166,452 A | 9/1979 | Generales, Jr. |
| 5,120,643 A | 6/1992 | Ching et al. |
| (Continued) | | |

FOREIGN PATENT DOCUMENTS

| CN | 101091700 | 12/2007 |
| EP | 0582368 B1 | 1/2001 |
| (Continued) | | |

OTHER PUBLICATIONS

Abdel-Baki, A., et al., "Pharmacotherapy Challenges in Patients with First-Episode Psychosis", Journal of Affective Disorders, vol. 138, pp. S3-S14 (2012).

(Continued)

*Primary Examiner* — Shafiqul Haq
(74) *Attorney, Agent, or Firm* — Fay Kaplun & Marcin, LLP

(57) ABSTRACT

Disclosed is an antibody or a binding fragment thereof which binds to quetiapine, which can be used to detect quetiapine in a sample such as in a competitive immunoassay method. The antibody or the fragment thereof can be used in a lateral flow assay device for point-of-care detection of quetiapine, including multiplex detection of aripiprazole, quetiapine, olanzapine, and risperidone in a single lateral flow assay device.

21 Claims, 23 Drawing Sheets

Specification includes a Sequence Listing.

Related U.S. Application Data

(60) Provisional application No. 62/268,924, filed on Dec. 17, 2015.

(56) References Cited

U.S. PATENT DOCUMENTS

| | | |
|---|---|---|
| 5,559,041 A | 9/1996 | Kang et al. |
| 5,587,458 A | 12/1996 | King et al. |
| 5,641,870 A | 6/1997 | Rinderknecht et al. |
| 5,714,389 A | 2/1998 | Charlton et al. |
| 5,761,894 A | 6/1998 | Evans et al. |
| 6,034,078 A | 3/2000 | Fairhurst et al. |
| 6,139,800 A | 10/2000 | Chandler |
| 6,228,660 B1 | 5/2001 | May et al. |
| 7,163,681 B2 | 1/2007 | Giles-Komar et al. |
| 7,416,700 B2 | 8/2008 | Buechler et al. |
| 7,772,240 B2 | 8/2010 | Bang-Andersen et al. |
| 7,901,949 B2 | 3/2011 | Raj |
| 8,058,405 B2 | 11/2011 | Demuth et al. |
| 8,088,594 B2 | 1/2012 | Salamone et al. |
| 9,012,648 B2 | 4/2015 | Haspeslagh et al. |
| 9,303,041 B2 | 4/2016 | Donahue et al. |
| 9,304,126 B2 | 4/2016 | Donahue et al. |
| 9,394,354 B2 | 7/2016 | Haspeslagh et al. |
| 9,410,972 B2 | 8/2016 | Hryhorenko et al. |
| 9,434,693 B2 | 9/2016 | Wall et al. |
| 9,453,002 B2 | 9/2016 | Ahmad et al. |
| 9,465,041 B2 | 10/2016 | Hryhorenko et al. |
| 9,494,607 B2 | 11/2016 | Hryhorenko et al. |
| 9,494,608 B2 | 11/2016 | Hryhorenko et al. |
| 9,504,682 B2 | 11/2016 | Lin et al. |
| 9,611,332 B2 | 4/2017 | Hryhorenko et al. |
| 9,664,700 B2 | 5/2017 | Hryhorenko et al. |
| 9,751,953 B2 | 9/2017 | Hryhorenko et al. |
| 9,795,685 B2 | 10/2017 | Lin et al. |
| 9,850,318 B2 | 12/2017 | Hryhorenko et al. |
| 2003/0087306 A1 | 5/2003 | Christensen et al. |
| 2003/0143233 A1 | 7/2003 | Goshorn et al. |
| 2003/0202975 A1 | 10/2003 | Tedder |
| 2004/0127489 A1 | 7/2004 | Pickar et al. |
| 2005/0163708 A1 | 7/2005 | Robinson et al. |
| 2006/0046967 A1 | 3/2006 | Satyam |
| 2006/0235005 A1 | 10/2006 | Goff |
| 2006/0251592 A1 | 11/2006 | Hendler et al. |
| 2006/0289787 A1 | 12/2006 | Ohman et al. |
| 2007/0231883 A1 | 10/2007 | Lindstrom et al. |
| 2008/0260812 A1 | 10/2008 | Matsuyama et al. |
| 2008/0261237 A1 | 10/2008 | Bazin et al. |
| 2009/0325193 A1 | 12/2009 | Grenier et al. |
| 2010/0069356 A1 | 3/2010 | Grant et al. |
| 2010/0144781 A1 | 6/2010 | Fu et al. |
| 2010/0203129 A1 | 8/2010 | Andersen et al. |
| 2010/0266502 A1 | 10/2010 | Kimura |
| 2011/0230520 A1 | 9/2011 | Sartor et al. |
| 2011/0245224 A1 | 10/2011 | Barvian et al. |
| 2012/0004165 A1 | 1/2012 | Keil et al. |
| 2012/0071636 A1 | 3/2012 | Salamone et al. |
| 2014/0057297 A1 | 2/2014 | Hryhorenko et al. |
| 2014/0057298 A1 | 2/2014 | Hryhorenko et al. |
| 2014/0057299 A1 | 2/2014 | Hryhorenko et al. |
| 2014/0057300 A1 | 2/2014 | Hryhorenko et al. |
| 2014/0057301 A1 | 2/2014 | Hryhorenko et al. |
| 2014/0057302 A1 | 2/2014 | Hryhorenko et al. |
| 2014/0057303 A1 | 2/2014 | Hryhorenko et al. |
| 2014/0057304 A1 | 2/2014 | Hryhorenko et al. |
| 2014/0057305 A1* | 2/2014 | Hryhorenko ........... G01N 33/94 435/7.93 |
| 2014/0057306 A1 | 2/2014 | Hryhorenko et al. |
| 2014/0155585 A1 | 6/2014 | Haspeslagh et al. |
| 2014/0162997 A1 | 6/2014 | Wall et al. |
| 2014/0163206 A1 | 6/2014 | Lin et al. |
| 2014/0213766 A1 | 7/2014 | Donahue et al. |
| 2014/0213767 A1 | 7/2014 | Haspeslagh et al. |
| 2014/0221616 A1 | 8/2014 | Donahue et al. |
| 2015/0051225 A1 | 2/2015 | Ahmad et al. |
| 2017/0045537 A1 | 2/2017 | Hryhorenko et al. |
| 2017/0176473 A1 | 6/2017 | Hryhorenko et al. |
| 2017/0299618 A1 | 10/2017 | Hryhorenko et al. |

FOREIGN PATENT DOCUMENTS

| | | |
|---|---|---|
| EP | 0583820 A1 | 3/2002 |
| EP | 2316468 A1 | 5/2011 |
| WO | WO 1995/34652 | 12/1995 |
| WO | WO 2003/082877 | 10/2003 |
| WO | WO 2003/103835 | 12/2003 |
| WO | WO 2004/014895 | 2/2004 |
| WO | WO 2005/000901 | 1/2005 |
| WO | WO 2005/028458 | 3/2005 |
| WO | WO 2005/033073 | 4/2005 |
| WO | WO 2005/041937 | 5/2005 |
| WO | WO 2005/089082 | 9/2005 |
| WO | WO 2005/118139 | 12/2005 |
| WO | WO 2006/137785 | 12/2006 |
| WO | WO 2008/050341 | 5/2008 |
| WO | WO 2008/073222 | 6/2008 |
| WO | WO 2009/040409 | 4/2009 |
| WO | WO 2010/015029 | 2/2010 |
| WO | WO 2010/033270 | 3/2010 |
| WO | WO 2010/104749 | 9/2010 |
| WO | WO 2011/082076 | 7/2011 |
| WO | WO 2011/112657 | 9/2011 |
| WO | WO 2011/115733 | 9/2011 |
| WO | WO 2011/159537 | 12/2011 |
| WO | WO 2012/003418 A2 | 1/2012 |
| WO | WO 2012/012595 A2 | 1/2012 |
| WO | WO 2013/088255 | 6/2013 |
| WO | WO 2014/031584 A1 | 2/2014 |
| WO | WO 2014/031587 A1 | 2/2014 |
| WO | WO 2014/031595 A1 | 2/2014 |
| WO | WO 2014/031600 A1 | 2/2014 |
| WO | WO 2014/031601 A1 | 2/2014 |
| WO | WO 2014/031603 A1 | 2/2014 |
| WO | WO 2014/031630 A2 | 2/2014 |
| WO | WO 2014/031635 A1 | 2/2014 |
| WO | WO 2014/031640 A2 | 2/2014 |
| WO | WO 2014/031645 A1 | 2/2014 |
| WO | WO 2014/031648 A2 | 2/2014 |
| WO | WO 2014/031656 A1 | 2/2014 |
| WO | WO 2014/031662 A2 | 2/2014 |
| WO | WO 2014/031665 A1 | 2/2014 |
| WO | WO 2014/031668 A2 | 2/2014 |
| WO | WO 2017/106501 A1 | 6/2017 |
| WO | WO 2017/106501 R3 | 6/2017 |
| WO | WO 2017/106508 A1 | 6/2017 |
| WO | WO 2017/106508 R3 | 6/2017 |

OTHER PUBLICATIONS

Aliouane, L., et al., "Synthesis of Difluoromethylphosphonamidates by Directed Addition of Amine", Tetrahedron Letters, vol. 52, pp. 3681-3685 (2011).

Alphs et al., "Onset of efficacy with acute long-acting injectable paliperidone palmitate treatment in markedly to severely ill patients with schizophrenia: post hoc analysis of a randomized, double-blind clinical trial," Annals of General Psychiatry, 2011, 10(12): 1-10.

Amit et al., Three-dimensional structure of an antigen-antibody complex at 2.8A resolution. Science, 1986, vol. 233, No. 4765, pp. 747-753.

Annuziato, M., et al., "p-Maleimidophenyl Isocyanate: A Novel Heterobifunctional Linker for Hydroxyl to Thiol Coupling", Bioconjugate Chemistry, vol. 4, pp. 212-218 (1993).

Billah, Md., et al. "Directed Immobilization of Reduced Antibody Fragments onto a Novel SAM on Gold for Myoglobin Impedance Immunosensing", Bioelectrochemistry, vol. 80, pp. 49-54 (2010).

Bodin, A., et al., "Identification and Allergenic Activity of Hydroxyaldehydes—A New Type of Oxidation Product from an Ethylated Non-Ionic Surfactant", Contact Dermatitis, vol. 44, pp. 207-212 (2001).

Brinkley, Michael, "A Brief Survey of Methods for Preparing Protein Conjugates with Dyes, Haptens, and Cross-Linking Reagents", Bioconjugate Chemistry, vol. 3, pp. 2-13 (1992).

(56) References Cited

OTHER PUBLICATIONS

Carter, P., et al., "High Level *Escherichia coli* Expression and Production of a Bivalent Humanized Antibody Fragment", Biotechnology, vol. 10, pp. 163-167.
Chamow, S., et al., "Conjugation of Soluble CD4 without Loss of Biological Activity via a Novel Carbohydrate-Directed Cross-Linking Reagent", The Journal of Biological Chemistry, vol. 267, No. 22, Issue of Aug. 5, pp. 15916-15922 (1992).
Chappey, O., et al., "Monoclonal Antibodies in Hapten Immunossays", Pharmaceutical Research, vol. 9, No. 11, pp. 1375-1379 (1992).
Cleland, W. W., Dithiothreitol, a New Protective Reagent for SH Groups, Biochemistry, vol. 3, No. 4, pp. 480-482 (1964).
Dai, R., et al., "A High-Throughput Assay for Evaluating State Dependence and Subtype Selectivity of Cav2 Calcium Channel Inhibitors", ASSAY and Drug Development Technologies, vol. 6, No. 2, pp. 195-212 (2008).
Danilova, N., et al., "Production and Characterization of Anti-Theophylline Monoclonal Antibodies Suitable for Immunoassay", Immunology Letters, vol. 29, pp. 79-84 (1991).
Davis, P., et al., "Development and Validation of an LC-MS/MS Method for the Determination of Quetiapine and Four Related Metabolites in Human Plasma", Journal of Pharmaceutical and Biomedical Analysis, vol. 51, pp. 1113-1119 (2010).
Diago-Meseguer, J., et al., "A New Reagent for Activating Carboxyl Groups, Preparation and Reactions of N,N-Bis[2-oxo-3-oxazolidinyl)phosphorodiamidic Chloride", Syntheses, vol. 7(1), pp. 547-551 (1980).
Dixon, W.J., "Efficient Analysis of Experimental Observations", Ann. Rev. Pharmacol. Toxicol., vol. 20, pp. 441-462 (1980).
Fiedler, H., et al., "Surface Chemical Characterization of Maleic Acid Mono[2-4-alkylpiperazinyl)ethyl esters]. 1. The Complex Adsorption Behavior of an Ampholytic Surfactant", Langmuir, vol. 10 pp. 3959-3965 (1994).
Finley, F., et al., "An Integrated Multiassay Approach to the Discovery of Small-Molecule N-Type Voltage-Gated Calcium Channel Antagonists", ASSAY and Drug Development Technologies, vol. 8, No. 6, pp. 685-694 (2010).
GENTAUR Molecular Products, ID Labs, IDEL-F083 Data Sheet, Enzyme Immunoassay for the Detection of Olanzapine in Urine or Serum, 1-6 (May 2012).
Ghetie, V., et al., "Preparation and Characterization of Conjugates of Recombinant CD4 and Deglycosylated Ricin A Chain Using Different Cross-Linkers", Bioconugate Chemistry, vol. 1, pp. 24-31 (1990).
Goodrow et al., "Strategies for immunoassay hapten design," Immunoanalysis of Agrochemicals 1995, ACS symposium Series, Chapter 9, vol. 586, pp. 119-139.
Gorja, D., et al., "Novel N-lndolylmethyl Substituted Olanzapine Derivatives: Their Design, Synthesis and Evaluation as PDE4B Inhibitors+", Organic & Bimolecular Chemistry, vol. 11, pp. 2075-2079 (2013).
Heykants, J., et al., "The Pharmacokinetics of Risperidone in Humans: A Summary", J. Clinical Psychiatry, vol. 55(5), pp. 13-17 (1994).
Huang, M-L, et al., "Pharmacokinetics of the Novel Antipsychotic Agent Risperidone and the Prolactin Response in Healthy Subjects", Clinical Pharmacology Therapeutics, vol. 54, pp. 257-268 (1993).
Huse, W., et al., Generation of a Large Combinatorial Library of the Immunoglobulin Repertoire in Phage Lambda, Research Article, pp. 1275-1281 (Dec. 1989).
International Search Report dated Jan. 16, 2014 for Application No. PCT/US2013/055775.
International Search Report dated Mar. 10, 2014 for Application No. PCT/US2013/055787.
International Search Report dated Mar. 10, 2014 for Application No. PCT/US2013/055803.
International Search Report dated Mar. 3, 2014 for Application No. PCT/US2013/055826.
International Search Report dated Mar. 4, 2014 for Application No. PCT/US2013/055834.
International Search Report dated Oct. 31, 2013 for Application No. PCT/US2013/055282.
International Search Report dated Oct. 11, 2013 for Application No. PCT/US2013/055263.
Kim, J., et al., Competitive enzyme-linked immunosorbent assay for the determination of catecholamine, dopamine in serum, Anal Chimica Acta. 2008; 619(1):87-93.
Kim, S., et al., "An Experimental Model for Peripheral Neuropathy Produced by Segmental Spinal Nerve Ligation in the Rat", Pain, vol. 50, pp. 355-363 (1992).
Kirley, Terence L., Reduction and Fluorescent Labeling of Cyst€ine-Containing Proteins for Subsequent Structural Analyses, Analytical Biochemistry, vol. 180, pp. 231-236 (1989).
Kohler, C., et al., "Continuous Cultures of Fused Cells Secreting Antibody of Predefined Specificity", Nature, vol. 256, Aug. 7, 1975 pp. 495-497.
Konig, W., et al., "A New Method for Synthesizing Peptides: Activation of Carboxyl Molecules With Dicyclohexylcarbodiimide by Adding 1-Hydroxybenzopartriazles", Chem. Ber. vol. 103, pp. 788-798 (1970).
Li, Z., et al., "Synthesis and Characteristization of N-Benzoyl-N'-Carboxyalkyl Substituted Thiourea Derivatives", Phosphorus, Sulfur and Silicon, vol. 178, pp. 293-297 (2003).
Lieberman, J., et al., "Effectiveness of Antipsychotic Drugs in Patients with Chronic Schizophrenia", The New England Journal of Medicine, vol. 353, pp. 1209-1223 (2005).
Liu, H., et al., "Organophosphorus Compound DEPBT as a Coupling Reagent for Oligopeptides and Peptoids Synthesis: Studies on Its Mechanism", Chinese Chemical Letters, vol. 13, No. 7, pp. 601-604 (2002).
Liu, W. et al., Preparation of monoclonal antibody and development of an indirect competitive ELISA for the detection of chlorpromazine residue in chicken and swine liver, J. Sci. Food Agric., 2010; 90:1789-1795.
Maddox, D., et al., "Elevated Serum Levels in Human Pregnancy of a Molecule Immunochemically Similar to Eospiophil Granule major Basic Protein", J. Exp. Medicine, vol. 158, pp. 1211-1226 (1983).
Malachowski, W., et al. The Chemistry of Phosphapeptides: Formation of Functionalized Phosphonochloridates Under Mild Conditions and Their Reaction With Alcohols and Amines, Journal of Organic Chemistry, vol. 59, pp. 7616-7624 (1994).
Mandrioli et al. HPLC analysis of the novel antipsychotic drug quetiapine in human plasma. J. Phar. & Biochemical Analysis 2002, vol. 30, pp. 969-977.
McKay, G., et al., Development and Application of Radioimmunoassay for Fluphenazine Based on Monoclonal Antibodies and its Comparison with Alternative Assay Methods, 1990; 79(3):240-243.
Modena, D., et al, Production and Characterization of Murne Monoclonal Antibodies to Polypeptide Hormones and Their Fragments, Annali Dell'lstitto Superiore di Sanita, vol. 27, No. 1, pp. 167-174 (1991).
Needleman, S., et al., "A General Method Applicable to the Search for Similarities in the Amino Acid Sequence of Two Proteins", J. Molecular Biology, vol. 48, pp. 443-453 (1970).
Nielsen, C., et al., "Anti-Allodynic Efficacy of the x-Conopeptide, Xen2174, in Rats with Neuropathic Pain", Pain, vol. 118, p. 112-124 (2005).
Nolli, M., et al., "Antibodies Against the Antibiotics: An Overview", Annali, Istituto Superiore di Sanita, vol. 27, No. 1, pp. 149-154 (1991).
Pan, R-N., et al., Validated LC-MS/MS Method of Determination of Quetiapine in Human Plasma: Application to a Pharmacokinetic Study, J. Chromatogr. Sci., 2012; 50:277-282.
Park, J., et al., "Novel Cyanine Dyes with Vinylsulfone Group for Labeling Biomolecules", Bioconjugate Chemistry, pp. 350-362 (2012).
Penning, T., et al., "Synthesis of Potent Leukotriene A4 Hydrolase Inhibitors. Identification of 3-[Methyl]4-(phenhlmethyl)phenooxy]propyl]amino]propanoic Acid", J. Medical Chemistry, vol. 45, pp. 3482-3490 (2002).

(56) References Cited

OTHER PUBLICATIONS

Posthuma-Trumpie et al., "Lateral flow (immuno) assay: its strength, weakness, opportunities and threats. A literature survey", Anal Bioanal Chem, 2009; 393:569-582.

Pruhs, S., et al., "Upscaling the Solid-Phase Synthesis of a Tetrahydrocarabazole in Chemical Development" Organic Process Research & Development, vol. 10, pp. 441-445 (2006).

Rudikoff et al., "Single Amino Acid Substitution Altering Antigen-Binding Specificity", PNAS, vol. 79, pp. 1979-1983 (1982).

Schmid, K., et al., "Distribution of Cyclopropenoid Fatty Acids in Malvaceous Plant Parts", Phytochemistry, vol. 27, No. 9, pp. 2831-2834 (1988).

Smith, T., et al., "Comparison of Biosequences", Advances in Applied Mathematics, vol. 2, pp. 482-489 (1981).

Su, J., et al., "Modification of the Clozapine structure by Parallel Synthesis", Bioorganic & Medicinal Chemistry Letters, vol. 16, p. 4548-4553 (2006).

Subasinghe, N., et al., "A Novel Series of Pyrazolylpiperidine N-Type Calcium Channel Blockers", Bioorganic & Medicinal Chemistry Letters, vol. 22, pp. 4080-4083 (2012).

Tu, Ju-Ying, et al., UPLC-MS-MS Analysis of Quetiapine and its two active metabolites, 7-hydroxyquetiapine and 7-hydroxy-N-dealkylquetiapine, in rat plasma and cerebrospional fluid, Chromatographia, 2008; 68:525-532.

Van Os, J., et al., "Schizophrenia", Lancet, vol. 374, pp. 635-645 (2009).

Warava, E. J., et al., "Behavioral Approach to Nondyskinetic dopamine antagonists: identification of Seroquel", J. Med. Chem., 2001; 44(3):373.

Westermann, et al., "Simple, rapid and sensitive determination of epinephrine and norepinephrine in urine and plasma by non-competitive enzyme immunoassay, compared with HPLC method", Clin. Lab., 2002; 48:61-71.

Wilbur, D., et al., Reagents for Astatination of Biomolecules; Comparison of the In Vivo Distribution and Stability of Some Radioiodinated/Astatinated Benzamidyl and nido-Carboranyl Compounds, Bioconjugate Chemistry, vol. 15, pp. 203-223 (2004).

Wring, S. et al. "Shorter development of immunoassay for drugs: application of the novel RIMMS technique enables rapid production of monoclonal antibodies to ranitidine." Journal of Pharmaceutical and Biomedical Analysis, 1999; vol. 19, No. 1: 695-707.

Woestenborghs, R., et al, "On the Selectivity of Some Recently Developed RIA's", Methodological Surveys in Biochemistry and Analysis. vol. 20, pp. 241-246 (1990).

Wu, X., et al. "A New Homobifunctional p-Nitro Phenyl Ester XCoupling Reagent for the Preparation of Neoglycoproteins", Organic Letters, vol. 6, No. 24, pp. 4407-4410 (2004).

Zhou, et al., "Simultaneous determination of clozapine, olanzapine, risperidone and quetiapine in plasma by high-performance liquid chromatography-electrospray ionization mass spectrometry", J Chromatogr. B. 2004; 802:257-262.

\* cited by examiner

US 11,104,742 B2

1

ANTIBODIES TO QUETIAPINE AND USE THEREOF

SEQUENCE LISTING

This application contains a Sequence Listing that has been submitted electronically in ASCII format and is hereby incorporated by reference in its entirety. Said ASCII copy, created Dec. 12, 2016, is named PRD3398USNP_SL.txt and is 18,376 bytes in size.

CROSS-REFERENCE TO RELATED APPLICATIONS

This application is a Continuation application of U.S. patent application Ser. No. 15/380,729 filed on Dec. 15, 2016, which claims benefit of U.S. Provisional Application Ser. No. 62/268,924, filed Dec. 17, 2015. The entire content of the above applications/patents is incorporated by reference herein.

FIELD OF THE INVENTION

The present invention relates to the field of immunoassays, and in particular to antibodies that bind to quetiapine which can be used in immunoassays for detection of quetiapine.

BACKGROUND

Schizophrenia is a chronic and debilitating psychiatric disorder affecting approximately 0.45-1% of the world's population (van Os, J.; Kapur, S. "Schizophrenia" Lancet 2009, 374, 635-645). The principal goals of treatment are to achieve sustained remission from psychotic symptoms, reduce the risk and consequences of relapse, and improve patient functioning and overall quality of life. While many patients with schizophrenia are able to achieve symptom stability with the available antipsychotic medications, poor adherence to medication is a common reason for relapse with daily administered oral medications. Several studies (Abdel-Baki, A.; Ouellet-Plamondon, C.; Malla, A. "Pharmacotherapy Challenges in Patients with First-Episode Psychosis" Journal of Affective Disorders 2012, 138, S3-S14) investigating the outcomes of non-compliance have shown that patients with schizophrenia who do not take their medication as prescribed have higher rates of relapse, hospital admission and suicide as well as increased mortality. It is estimated that 40 to 75% of patients with schizophrenia have difficulty adhering to a daily oral treatment regimen (Lieberman, J. A.; Stroup, T. S.; McEvoy, J. P.; Swartz, M. S.; Rosenheck, R. A.; Perkins, D. O.; Keefe, R. S. E.; Davis, S. M.; Davis, C. E.; Lebowitz, B. D.; Severe, J.; Hsiao, J. K. "Effectiveness of Antipyschotic Drugs in Patients with Chronic Schizophrenia" New England Journal of Medicine 2005, 353(12), 1209-1223).

Therapeutic drug monitoring (TDM) is the quantification of serum or plasma concentrations of drugs, including anti-psychotic drugs, for treatment monitoring and optimization. Such monitoring permits, for example, the identification of patients that are not adhering to their medication regimen, that are not achieving therapeutic doses, that are non-responsive at therapeutic doses, that have suboptimal tolerability, that have pharmacokinetic drug-drug interactions, or that have abnormal metabolism resulting in inappropriate plasma concentrations. Considerable individual variability exists in the patient's ability to absorb, distribute, metabolize, and excrete anti-psychotic drugs. Such differences can be caused by concurrent disease, age, concomitant medication or genetic peculiarities. Different drug formulations can also influence the metabolism of anti-psychotic drugs. TDM permits dose optimization for individual patients, improving therapeutic and functional outcomes. TDM further permits a prescribing clinician to ensure compliance with prescribed dosages and achievement of effective serum concentrations.

To date, methods for determining the levels of serum or plasma concentrations of anti-psychotic drugs involve the use of liquid chromatography (LC) with UV or mass spectrometry detection, and radioimmunoassays (see, for example, Woestenborghs et al., 1990 "On the selectivity of some recently developed RIA's" in Methodological Surveys in Biochemistry and Analysis 20:241-246. Analysis of Drugs and Metabolites, Including Anti-infective Agents; Heykants et al., 1994 "The Pharmacokinetics of Risperidone in Humans: A Summary", J Clin Psychiatry 55/5, suppl:13-17; Huang et al., 1993 "Pharmacokinetics of the novel anti-psychotic agent risperidone and the prolactin response in healthy subjects", Clin Pharmacol Ther 54:257-268). Radioimmunoassays detect one or both of risperidone and paliperidone. Salamone et al. in U.S. Pat. No. 8,088,594 disclose a competitive immunoassay for risperidone using antibodies that detect both risperidone and paliperidone but not pharmacologically inactive metabolites. The antibodies used in the competitive immunoassay are developed against a particular immunogen. ID Labs Inc. (London, Ontario, Canada) markets an ELISA for olanzapine, another antipsychotic drug, which also utilizes a competitive foimat. The Instructions For Use indicate that the assay is designed for screening purposes and intended for forensic or research use, and is specifically not intended for therapeutic use. The Instructions recommend that all positive samples should be confirmed with gas chromatography/mass spectrometry (GC-MS), and indicate that the antibody used detects olanzapine and clozapine (see ID Labs Inc., "Instructions For Use Data Sheet IDEL-F083", Rev. Date Aug. 8, 2011). Some of these methods, namely HPLC and GC/MS, can be expensive and labor-intensive, and are generally only performed in large or specialty labs having the appropriate equipment.

A need exists for other methods for determining the levels of anti-psychotic drugs, particularly methods that can be performed in a prescribing clinician's office (where the treatment for an individual patient can be adjusted accordingly in a much more timely manner) and in other medical settings lacking LC or GC/MS equipment or requiring rapid test results.

SUMMARY OF THE INVENTION

The present invention is directed to an isolated antibody or a binding fragment thereof, which binds to quetiapine and which is an isolated antibody or binding fragment thereof selected from the group consisting of: a) an isolated antibody or a fragment thereof comprising a heavy chain variable region, and a light chain variable region comprising an amino acid sequence selected from the group consisting of SEQ ID NO:3, SEQ ID NO:8, SEQ ID NO:9, SEQ ID NO:13 and SEQ ID NO:17; b) an isolated antibody or a fragment thereof comprising a heavy chain variable region comprising an amino acid sequence selected from the group consisting of SEQ ID NO:4, SEQ ID NO:10, SEQ ID NO:14 and SEQ ID NO:18, and a light chain variable region; c) an isolated antibody or a fragment thereof comprising a light chain variable region having an amino acid sequence of SEQ 1D NO:3 and a heavy chain variable region having an amino acid sequence of SEQ ID NO:4; d) an isolated antibody or a fragment thereof comprising a light chain variable region having an amino acid sequence of SEQ ID NO:8 and a heavy chain variable region having an amino acid sequence of SEQ ID NO:10; e) an isolated antibody or a fragment thereof comprising a light chain variable region having an amino acid sequence of SEQ ID NO:9 and a heavy chain variable region having an amino acid sequence of SEQ ID NO:10; 0 an isolated antibody or a fragment thereof comprising a light chain variable region having an amino acid sequence of SEQ ID NO:13 and a heavy chain variable region having an amino acid sequence of SEQ ID NO:14; and g) an isolated antibody or a fragment thereof comprising a light chain variable region having an amino acid sequence of SEQ ID NO:17 and a heavy chain variable region having an amino acid sequence of SEQ ID NO:18.

An embodiment of the invention is an isolated antibody or a binding fragment thereof, which binds to quetiapine comprising: a) an isolated antibody or a fragment thereof comprising a light chain variable region having an amino acid sequence of SEQ ID NO:3 and a heavy chain variable region having an amino acid sequence of SEQ ID NO:4; b) an isolated antibody or a fragment thereof comprising a light chain variable region having an amino acid sequence of SEQ ID NO:8 and a heavy chain variable region having an amino acid sequence of SEQ ID NO:10; c) an isolated antibody or a fragment thereof comprising a light chain variable region having an amino acid sequence of SEQ ID NO:9 and a heavy chain variable region having an amino acid sequence of SEQ ID NO:10; d) an isolated antibody or a fragment thereof comprising a light chain variable region having an amino acid sequence of SEQ ID NO:13 and a heavy chain variable region having an amino acid sequence of SEQ ID NO:14; or e) an isolated antibody or a fragment thereof comprising a light chain variable region having an amino acid sequence of SEQ ID NO:17 and a heavy chain variable region having an amino acid sequence of SEQ ID NO:18.

The present invention further is directed to an isolated antibody or a binding fragment thereof, which competes for an epitope that is capable of binding the isolated antibody or binding fragment thereof identified above, and which is the same as an epitope bound by the antibody identified above.

In a further embodiment, the present invention is directed to an isolated antibody or a binding fragment thereof, which binds to quetiapine and which comprises a light chain variable region comprising an amino acid sequence having at least 80% sequence identity with SEQ ID NO:3, SEQ ID NO:8, SEQ ID NO:9, SEQ ID NO:13 or SEQ ID NO:17. In embodiments, the light chain variable region comprises an amino acid sequence having at least 85% sequence identity, at least 90% sequence identity, at least 95% sequence identity, at least 96% sequence identity, at least 97% sequence identity, at least 98% sequence identity, or at least 99% sequence identity with SEQ ID NO:3, SEQ ID NO:8, SEQ ID NO:9, SEQ ID NO:13 or SEQ ID NO:17.

In a further embodiment, the present invention is directed to an isolated antibody or a binding fragment thereof, which binds to quetiapine and which comprises a heavy chain variable region comprising an amino acid sequence having at least 80% sequence identity with SEQ ID NO:4, SEQ ID NO:10, SEQ ID NO:14 or SEQ ID NO:18. In embodiments, the heavy chain variable region comprises an amino acid sequence having at least 85% sequence identity, having at least 90% sequence identity, at least 95% sequence identity, at least 96% sequence identity, at least 97% sequence identity, at least 98% sequence identity, or at least 99% sequence identity with SEQ ID NO:4, SEQ ID NO:10, SEQ ID NO:14 or SEQ ID NO:18.

Additional embodiments of the antibody or binding fragment thereof of the subject invention described herein are: an antibody or binding fragment thereof which comprises a light chain variable region and a heavy chain variable region, wherein the light chain variable region is selected from the group consisting of: a) a light chain variable region having a complementarity determining region 1 (CDR1) sequence comprising amino acid residues 43 to 58 of SEQ ID NO:3, a CDR2 sequence comprising amino acid residues 74 to 80 of SEQ ID NO:3, and a CDR3 sequence comprising amino acid residues 117 to 126 of SEQ ID NO:3; b) a light chain variable region having a CDR1 sequence comprising amino acid residues 43 to 58 of SEQ ID NO:8, a CDR2 sequence comprising amino acid residues 74 to 80 of SEQ ID NO:8, and a CDR3 sequence comprising amino acid residues 113 to 121 of SEQ ID NO:8; c) a light chain variable region having a CDR1 sequence comprising amino acid residues 46 to 56 of SEQ ID NO:9, a CDR2 sequence comprising amino acid residues 72 to 78 of SEQ ID NO:9, and a CDR3 sequence comprising amino acid residues 111 to 119 of SEQ ID NO:9; d) a light chain variable region having a CDR1 sequence comprising amino acid residues 43 to 58 of SEQ ID NO:13, a CDR2 sequence comprising amino acid residues 74 to 80 of SEQ ID NO:13, and a CDR3 sequence comprising amino acid residues 113 to 121 of SEQ ID NO:13; and e) a light chain variable region having a CDR1 sequence comprising amino acid residues 46 to 55 of SEQ ID NO:17, a CDR2 sequence comprising amino acid residues 71 to 77 of SEQ ID NO:17, and a CDR3 sequence comprising amino acid residues 110 to 118 of SEQ ID NO:17; and wherein the heavy chain variable region is selected from the group consisting of: a) a heavy chain variable region having a CDR1 sequence comprising amino acid residues 50 to 54 of SEQ ID NO:4, a CDR2 sequence comprising amino acid residues 70 to 84 of SEQ ID NO:4, and a CDR3 sequence comprising amino acid residues 117 to 126 of SEQ ID NO:4; b) a heavy chain variable region having a CDR1 sequence comprising amino acid residues 49 to 54 of SEQ ID NO:10, a CDR2 sequence comprising amino acid residues 69 to 84 of SEQ ID NO:10, and a CDR3 sequence comprising amino acid residues 117 to 119 of SEQ ID NO:10; c) a heavy chain variable region having a CDR1 sequence comprising amino acid residues 50 to 54 of SEQ ID NO:14, a CDR2 sequence comprising amino acid residues 70 to 85 of SEQ ID NO:14, and a CDR3 sequence comprising amino acid residues 118 to 129 of SEQ ID NO:14; and d) a heavy chain variable region having a CDR' sequence comprising amino acid residues 50 to 54 of SEQ ID NO:18, a CDR2 sequence comprising amino acid residues 69 to 85 of SEQ ID NO:18, and a CDR3 sequence comprising amino acid residues 118 to 128 of SEQ ID NO:18.

The antibodies or binding fragments thereof of the invention can be provided in assay kits and assay devices, with a presently preferred device being a lateral flow assay device which provides for point-of-care analysis.

In preferred embodiments, the antibody is a monoclonal antibody. In some preferred embodiments, the antibody binding fragment is selected from the group of fragments consisting of Fv, F(ab'), F(ab')2, seFv, minibody and diabody fragments.

The invention further provides a method of detecting quetiapine in a sample. The method comprises: (i) contacting a sample with an antibody or binding fragment thereof according to the invention which is labeled with a detectable marker, wherein the labeled antibody and quetiapine present in the sample form a labeled complex; and (ii) detecting the labeled complex so as to detect quetiapine in the sample.

Further provided is a competitive immunoassay method for detecting quetiapine in a sample. The method comprises: (i) contacting a sample with an antibody or binding fragment thereof according to the invention, and with quetiapine or a competitive binding partner of quetiapine, wherein one of the antibody and the quetiapine or competitive binding partner thereof is labeled with a detectable marker, and wherein sample quetiapine competes with the quetiapine or competitive binding partner thereof for binding to the antibody or binding fragment thereof; and (ii) detecting the label so as to detect sample quetiapine.

Further objects, features and advantages of the present invention will be apparent to those skilled in the art from detailed consideration of the preferred embodiments that follow.

DETAILED DESCRIPTION

Figure 1A:
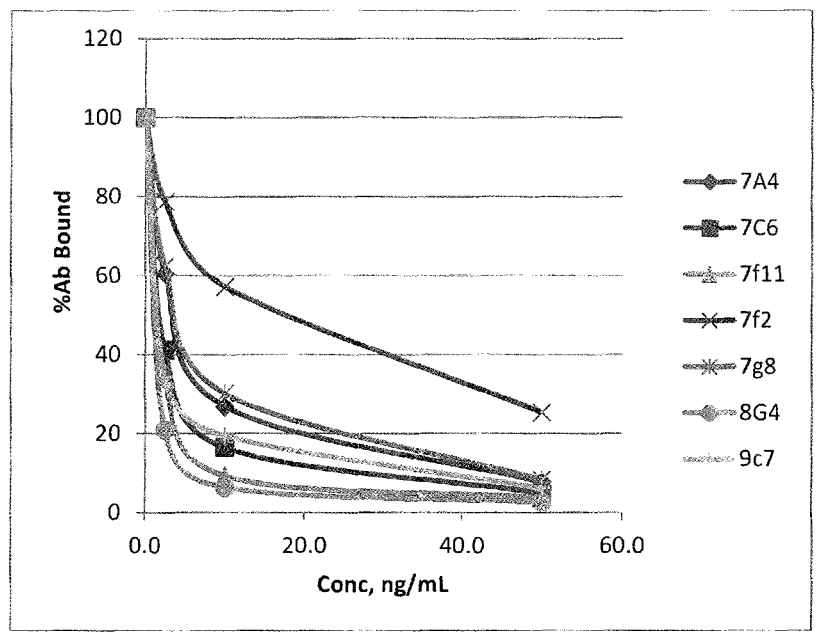
FIGS. 1A-1E show competitive ELISA results generated with various quetiapine hybridomas.
Figure 1B:
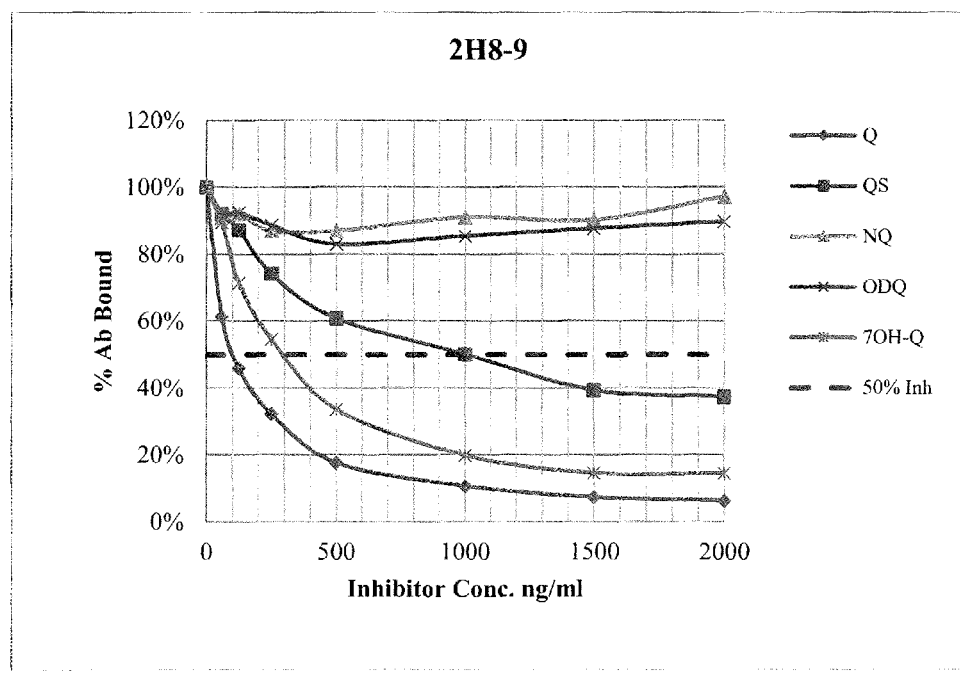
Figure 1C:
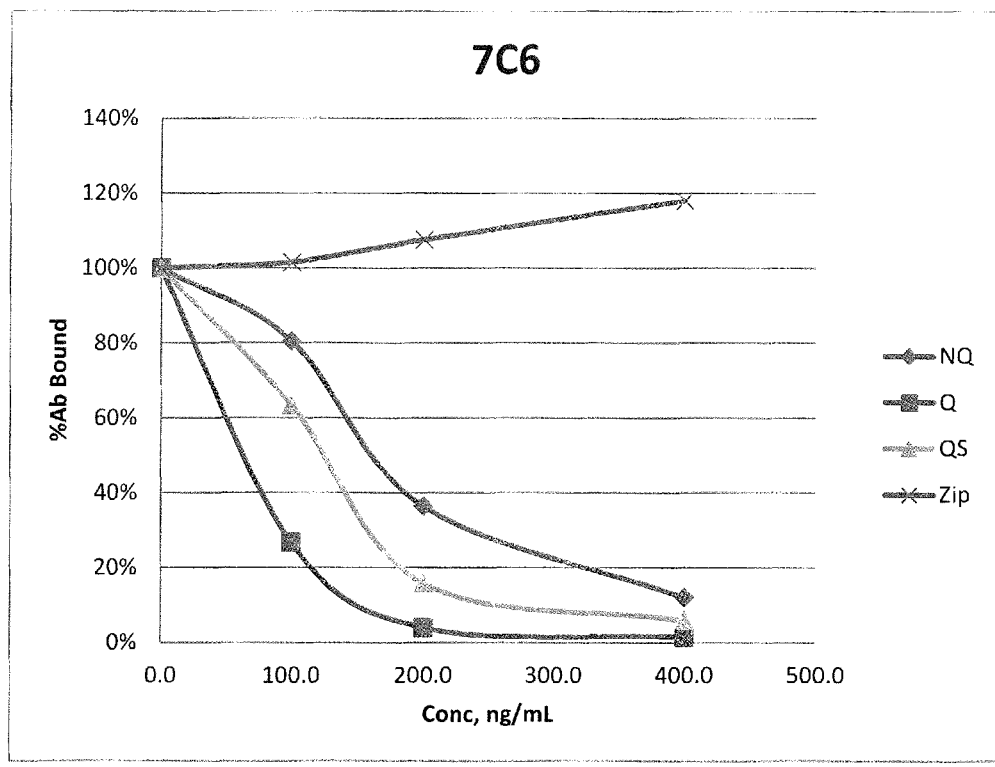
Figure 1D:
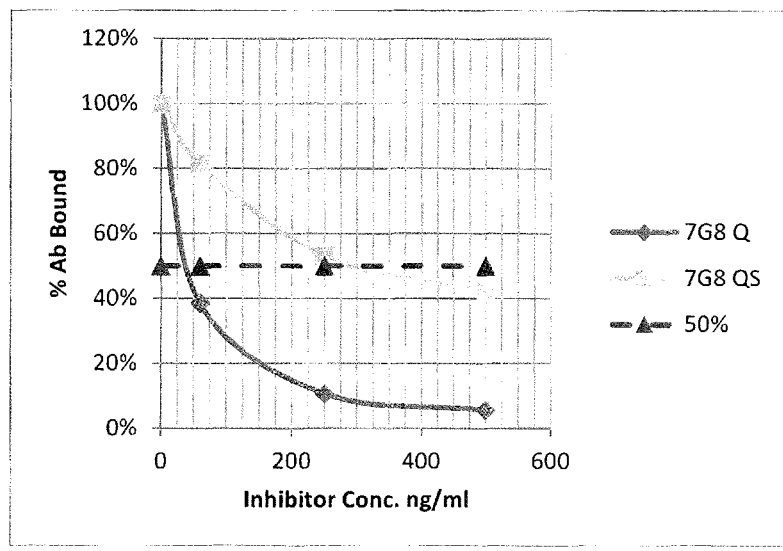
Figure 1E:
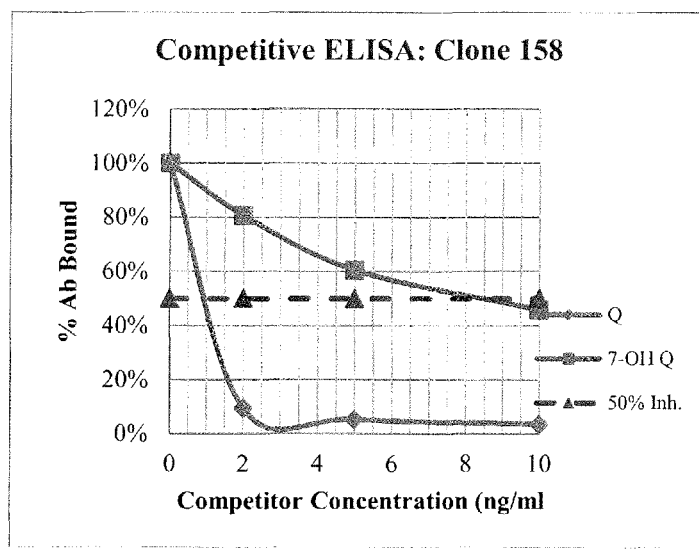

It is to be understood that this invention is not limited to particular methods, reagents, compounds, compositions or biological systems, which can, of course, vary. It is also to be understood that the terminology used herein is for the purpose of describing particular embodiments only, and is not intended to be limiting.

As used in this specification and the appended claims, the singular forms "a", and "the" include plural referents unless the content clearly dictates otherwise.

The following terms are used to describe the sequence relationships between two or more polynucleotide or amino acid sequences: "reference sequence", "comparison window", "sequence identity", "percentage of sequence identity", "substantial identity", "similarity", and "homologous". A "reference sequence" is a defined sequence used as a basis for a sequence comparison; a reference sequence may be a subset of a larger sequence, for example, a segment of a full length cDNA or gene sequence given in a sequence listing or may comprise a complete cDNA or gene sequence; a reference sequence may comprise a segment of a complete amino acid sequence encoding a protein as given in a sequence listing or may comprise a complete amino acid sequence encoding a protein. Generally, a reference sequence is at least 18 nucleotides or 6 amino acids in length, frequently at least 24 nucleotides or 8 amino acids in length, and often at least 48 nucleotides or 16 amino acids in length. Since two polynucleotide or amino acid sequences may each (1) comprise a sequence (i.e., a portion of the complete nucleotide or amino acid sequence) that is similar between the two molecules, and (2) may further comprise a sequence that is divergent between the two polynucleotide or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein the polynucleotide sequence or amino acid sequence may be compared to a reference sequence of at least 18 contiguous nucleotides or 6 amino acids and wherein the portion of the polynucleotide sequence or amino acid sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman, Adv. Appl. Math 2:482 (1981), by the homology alignment algorithm of Needlemen and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package Release 7.0 (Genetics Computer Group, 575 Science Dr., Madison, Wis.), Geneworks or MacVector software packages), or by inspection, and the best alignment (i.e., resulting in the highest percentage of identity over the comparison window) generated by the various methods is selected.

The temi "sequence identity" means that two polynucleotide or amino acid sequences are identical (i.e., on a nucleotide-by-nucleotide or amino acid residue-by-residue basis) over the comparison window. The term "percentage of sequence identity" is calculated by comparing two optimally aligned sequences over the window of comparison, determining the number of positions at which the identical nucleic acid base (e.g., A, T, C, G, or U) or amino acid residue occurs in both sequences to yield the number of matched positions, dividing the number of matched positions by the total number of positions in the comparison window (i.e., the window size), and multiplying the result by 100 to yield the percentage of sequence identity. The term "substantial identity" or "substantially identical" as used herein denotes a characteristic of a polynucleotide or amino acid sequence, wherein the polynucleotide or amino acid sequence comprises a sequence that has at least 85 percent sequence identity, preferably at least 85 to 99 percent sequence identity, more preferably at least 90 to 95 percent sequence identity, particularly preferable at least 85, 86, 87, 88, 89, 90, 91, 92, 93, 94, or 95 percent sequence identity, more usually at least 96, 97, 98 or 99 percent sequence identity as compared to a reference sequence over a comparison window of at least 18 nucleotide (6 amino acid) positions, particularly over a window of at least 18-48 nucleotide (6-16 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence. The term "similarity", when used to describe a polypeptide, is determined by comparing the amino acid sequence and the conserved amino acid substitutions of one polypeptide to the sequence of a second polypeptide. The term "homologous", when used to describe a polynucleotide, indicates that two polynucleotides, or designated sequences thereof, when optimally aligned and compared, are identical, with appropriate nucleotide insertions or deletions, in at least 70% of the nucleotides, preferably from at least 70% to 99%, usually from at least 75% to 99%, particularly at least 75%, 76%, 77%, 78%, 79%, 80%, 81%, 82%, 83%, 84%, 85%, 86%, 87%, 88%, 89%, 90%, 91%, 92%, 93%, 94%, 95%, and more preferably at least 96%, 97%, 98%, 99% of the nucleotides.

A "label," "detector molecule," "reporter" or "detectable marker" as used herein is any molecule which produces, or can be induced to produce, a detectable signal. The label can be conjugated to an analyte, immunogen, antibody, or to another molecule such as a receptor or a molecule that can bind to a receptor such as a ligand, particularly a hapten or antibody. A label can be attached directly or indirectly by means of a linking or bridging moiety. Non-limiting examples of labels include radioactive isotopes (e.g., $^{125}$I), enzymes (e.g. β-galactosidase, peroxidase), enzyme fragments, enzyme substrates, enzyme inhibitors, coenzymes, catalysts, fluorophores (e.g., rhodamine, fluorescein isothiocyanate or FITC, or Dylight 649), dyes, chemiluminescers and luminescers (e.g., dioxetanes, luciferin), or sensitizers.

The invention provides an isolated antibody or binding fragment thereof which binds to quetiapine. The invention further provides an assay kit and an assay device comprising the antibody or binding fragment thereof. Further provided is a method of detecting quetiapine in a sample, including a competitive immunoassay method.

In one embodiment, the present invention is directed to an isolated antibody or a binding fragment thereof, which binds to quetiapine and which is an isolated antibody or binding fragment thereof selected from the group consisting of: a) an isolated antibody or a fragment thereof comprising a heavy chain variable region, and a light chain variable region comprising an amino acid sequence selected from the group consisting of SEQ ID NO:3, SEQ ID NO:8, SEQ ID NO:9, SEQ ID NO:13 an SEQ ID NO:17; b) an isolated antibody or a fragment thereof comprising a heavy chain variable region comprising an amino acid sequence selected from the group consisting of SEQ ID NO:4, SEQ ID NO:10, SEQ ID NO:14 or SEQ ID NO:18, and a light chain variable region; c) an isolated antibody or a fragment thereof comprising a light chain variable region having an amino acid sequence of SEQ ID NO:3 and a heavy chain variable region having an amino acid sequence of SEQ ID NO:4; d) an isolated antibody or a fragment thereof comprising a light chain variable region having an amino acid sequence of SEQ ID NO:8 and a heavy chain variable region having an amino acid sequence of SEQ ID NO:10; e) an isolated antibody or a fragment thereof comprising a light chain variable region having an amino acid sequence of SEQ ID NO:9 and a heavy chain variable region having an amino acid sequence of SEQ ID NO:10; f) an isolated antibody or a fragment thereof comprising a light chain variable region having an amino acid sequence of SEQ ID NO:13 and a heavy chain variable region having an amino acid sequence of SEQ ID NO:14; and g) an isolated antibody or a fragment thereof comprising a light chain variable region having an amino acid sequence of SEQ ID NO:17 and a heavy chain variable region having an amino acid sequence of SEQ ID NO:18.

A further embodiment of the invention is an isolated antibody or a binding fragment thereof, which binds to quetiapine comprising: a) an isolated antibody or a fragment thereof comprising a light chain variable region having an amino acid sequence of SEQ ID NO:3 and a heavy chain variable region having an amino acid sequence of SEQ ID NO:4; b) an isolated antibody or a fragment thereof comprising a light chain variable region having an amino acid sequence of SEQ ID NO:8 and a heavy chain variable region having an amino acid sequence of SEQ ID NO:10; c) an isolated antibody or a fragment thereof comprising a light chain variable region having an amino acid sequence of SEQ ID NO:9 and a heavy chain variable region having an amino acid sequence of SEQ ID NO:10; d) an isolated antibody or a fragment thereof comprising a light chain variable region having an amino acid sequence of SEQ ID NO:13 and a heavy chain variable region having an amino acid sequence of SEQ ID NO:14; or e) an isolated antibody or a fragment thereof comprising a light chain variable region having an amino acid sequence of SEQ ID NO:17 and a heavy chain variable region having an amino acid sequence of SEQ ID NO:18.

In another embodiment, the invention is directed to an isolated antibody or a binding fragment thereof, which binds to quetiapine and competes for an epitope that is capable of binding an isolated antibody or a binding fragment thereof comprising a light chain variable region comprising an amino acid sequence selected from the group consisting of SEQ ID NO:3, SEQ ID NO:8, SEQ ID NO:9, SEQ ID NO:13 an SEQ ID NO:17, and a heavy chain variable region comprising an amino acid sequence selected from the group consisting of SEQ ID NO:4, SEQ ID NO:10, SEQ ID NO:14 or SEQ ID NO:18, and which is the same as an epitope bound by the antibody comprising a light chain variable region comprising an amino acid sequence selected from the group consisting of SEQ ID NO:3, SEQ ID NO:8, SEQ ID NO:9, SEQ ID NO:13 an SEQ ID NO:17, and a heavy chain variable region comprising an amino acid sequence selected from the group consisting of SEQ ID NO:4, SEQ ID NO:10, SEQ ID NO:14 or SEQ ID NO:18.

In a further embodiment, the present invention is directed to an isolated antibody or a binding fragment thereof, which binds to quetiapine and which comprises a light chain variable region comprising an amino acid sequence having at least 80% sequence identity with SEQ ID NO:3, SEQ ID NO:8, SEQ ID NO:9, SEQ ID NO:13 or SEQ ID NO:17. In embodiments, the light chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:3, SEQ ID NO:8, SEQ ID NO:9, SEQ ID NO:13 or SEQ ID NO:17.

In a further embodiment, the present invention is directed to an isolated antibody or a binding fragment thereof, which binds to quetiapine and which comprises a heavy chain variable region comprising an amino acid sequence having at least 80% sequence identity with SEQ ID NO:4, SEQ ID NO:10, SEQ ID NO:14 or SEQ ID NO:18. In embodiments, the heavy chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:4, SEQ ID NO:10, SEQ ID NO:14 or SEQ ID NO:18.

Presently preferred embodiments of the antibody or binding fragment thereof of the invention are: an antibody or binding fragment thereof which comprises a light chain variable region having the amino acid sequence SEQ ID NO:3 and a heavy chain variable region having the amino acid sequence SEQ ID NO:4; an antibody or binding fragment thereof which comprises a light chain variable region having the amino acid sequence SEQ ID NO:8 and a heavy chain variable region having the amino acid sequence SEQ ID NO:10; an antibody or binding fragment thereof which comprises a light chain variable region having the amino acid sequence SEQ ID NO:9 and a heavy chain variable region having the amino acid sequence SEQ ID NO:10; an antibody or binding fragment thereof which comprises a light chain variable region having the amino acid sequence SEQ ID NO:13 and a heavy chain variable region having the amino acid sequence SEQ ID NO:14; and an antibody or binding fragment thereof which comprises a light chain variable region having the amino acid sequence SEQ ID NO:17 and a heavy chain variable region having the amino acid sequence SEQ ID NO:18.

In an embodiment, the present invention is directed to an isolated antibody or a binding fragment thereof, which binds to quetiapine and which comprises a light chain variable region comprising an amino acid sequence having at least 80% sequence identity with SEQ ID NO:3. In embodiments, the light chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:3.

In a further embodiment, the present invention is directed to an isolated antibody or a binding fragment thereof, which binds to quetiapine and which comprises a heavy chain variable region comprising an amino acid sequence having at least 80% sequence identity with SEQ ID NO:4. In embodiments, the heavy chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:4.

Presently preferred embodiments of the antibody of the subject invention are an antibody or binding fragment thereof which comprises a light chain variable region having the amino acid sequence SEQ ID NO:3 and a heavy chain variable region having the amino acid sequence SEQ ID NO:4. In embodiments, the light chain variable region comprises an amino acid sequence having at least 80% sequence identity with SEQ ID NO:3 and the heavy chain variable region comprising an amino acid sequence having at least 80% sequence identity with SEQ ID NO:4. In some embodiments the light chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:3, and the heavy chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:4.

In a further embodiment, the present invention is directed to an isolated antibody or a binding fragment thereof, which binds to quetiapine and which comprises a light chain variable region comprising an amino acid sequence having at least 80% sequence identity with SEQ ID NO:8 or SEQ ID NO:9. In embodiments, the light chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:8 or SEQ ID NO:9.

In a further embodiment, the present invention is directed to an isolated antibody or a binding fragment thereof, which binds to quetiapine and which comprises a heavy chain variable region comprising an amino acid sequence having at least 80% sequence identity with SEQ ID NO:10. In embodiments, the heavy chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:10.

Presently preferred embodiments of the antibody or binding fragment thereof of the invention are an antibody or binding fragment thereof which comprises a light chain variable region having the amino acid sequence SEQ ID NO:8 and a heavy chain variable region having the amino acid sequence SEQ ID NO:10. In embodiments, the light chain variable region comprises an amino acid sequence having at least 80% sequence identity with SEQ ID NO:8 and the heavy chain variable region comprising an amino acid sequence having at least 80% sequence identity with SEQ ID NO:10. In some embodiments the light chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:8, and the heavy chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:10.

Other preferred embodiments of the antibody or binding fragment thereof of the invention are an antibody or binding fragment thereof which comprises a light chain variable region having the amino acid sequence SEQ ID NO:9 and a heavy chain variable region having the amino acid sequence SEQ ID NO:10. In embodiments, the light chain variable region comprises an amino acid sequence having at least 80% sequence identity with SEQ ID NO:9 and the heavy chain variable region comprising an amino acid sequence having at least 80% sequence identity with SEQ ID NO:10. In some embodiments the light chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:9, and the heavy chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ 1D NO:10.

In another embodiment, the present invention is directed to an isolated antibody or a binding fragment thereof, which binds to quetiapine and which comprises a light chain variable region comprising an amino acid sequence having at least 80% sequence identity with SEQ ID NO:13. In embodiments, the light chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:13.

In a further embodiment, the present invention is directed to an isolated antibody or a binding fragment thereof, which binds to quetiapine and which comprises a heavy chain variable region comprising an amino acid sequence having at least 80% sequence identity with SEQ ID NO:14. In embodiments, the heavy chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:14.

Presently preferred embodiments of the antibody or binding fragment thereof of the subject invention are an antibody or binding fragment thereof which comprises a light chain variable region having the amino acid sequence SEQ ID NO:13 and a heavy chain variable region having the amino acid sequence SEQ ID NO:14. In embodiments, the light chain variable region comprises an amino acid sequence having at least 80% sequence identity with SEQ ID NO:13 and the heavy chain variable region comprising an amino acid sequence having at least 80% sequence identity with SEQ ID NO:14. In some embodiments the light chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:13, and the heavy chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:14.

In another embodiment, the present invention is directed to an isolated antibody or a binding fragment thereof, which binds to quetiapine and which comprises a light chain variable region comprising an amino acid sequence having at least 80% sequence identity with SEQ ID NO:17. In embodiments, the light chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:17.

In a further embodiment, the invention is directed to an isolated antibody or a binding fragment thereof, which binds to quetiapine and which comprises a heavy chain variable region comprising an amino acid sequence having at least 80% sequence identity with SEQ ID NO:18 In embodiments, the heavy chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:18.

Additional embodiments of the antibody or binding fragment thereof of the invention are an antibody or binding fragment thereof which comprises a light chain variable region having the amino acid sequence SEQ ID NO:17 and a heavy chain variable region having the amino acid sequence SEQ ID NO:18. In embodiments, the light chain variable region comprises an amino acid sequence having at least 80% sequence identity with SEQ ID NO:17 and the heavy chain variable region comprising an amino acid sequence having at least 80% sequence identity with SEQ ID NO:18. In some embodiments the light chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:17, and the heavy chain variable region comprises an amino acid sequence at least 85% sequence identity, having at least 90% sequence identity, at least 95% sequence identity, at least 96% sequence identity, at least 97% sequence identity, at least 98% sequence identity, or at least 99% sequence identity with SEQ ID NO:18.

Further preferred embodiments of the antibody or binding fragment thereof of the subject invention are: an antibody or binding fragment thereof which comprises a light chain variable region and a heavy chain variable region, wherein the light chain variable region is selected from the group consisting of: a) a light chain variable region having a complementarity determining region 1 (CDR1) sequence comprising amino acid residues 43 to 58 of SEQ ID NO:3, a CDR2 sequence comprising amino acid residues 74 to 80 of SEQ ID NO:3, and a CDR3 sequence comprising amino acid residues 117 to 126 of SEQ ID NO:3; b) a light chain variable region having a CDR1 sequence comprising amino acid residues 43 to 58 of SEQ ID NO:8, a CDR2 sequence comprising amino acid residues 74 to 80 of SEQ ID NO:8, and a CDR3 sequence comprising amino acid residues 113 to 121 of SEQ ID NO:8; c) a light chain variable region having a CDR1 sequence comprising amino acid residues 46 to 56 of SEQ ID NO:9, a CDR2 sequence comprising amino acid residues 72 to 78 of SEQ ID NO:9, and a CDR3 sequence comprising amino acid residues 111 to 119 of SEQ ID NO:9; d) a light chain variable region having a CDR1 sequence comprising amino acid residues 43 to 58 of SEQ ID NO:13, a CDR2 sequence comprising amino acid residues 74 to 80 of SEQ ID NO:13, and a CDR3 sequence comprising amino acid residues 113 to 121 of SEQ ID NO:13; and e) a light chain variable region having a CDR1 sequence comprising amino acid residues 46 to 55 of SEQ ID NO:17, a CDR2 sequence comprising amino acid residues 71 to 77 of SEQ ID NO:17, and a CDR3 sequence comprising amino acid residues 110 to 118 of SEQ ID NO:17; and wherein the heavy chain variable region is selected from the group consisting of: a) a heavy chain variable region having a CDR1 sequence comprising amino acid residues 50 to 54 of SEQ ID NO:4, a CDR2 sequence comprising amino acid residues 70 to 84 of SEQ ID NO:4, and a CDR3 sequence comprising amino acid residues 117 to 126 of SEQ ID NO:4; b) a heavy chain variable region having a CDR1 sequence comprising amino acid residues 49 to 54 of SEQ ID NO:10, a CDR2 sequence comprising amino acid residues 69 to 84 of SEQ ID NO:10, and a CDR3 sequence comprising amino acid residues 117 to 119 of SEQ ID NO:10; c) a heavy chain variable region having a CDR1 sequence comprising amino acid residues 50 to 54 of SEQ ID NO:14, a CDR2 sequence comprising amino acid residues 70 to 85 of SEQ ID NO:14, and a CDR3 sequence comprising amino acid residues 118 to 129 of SEQ ID NO:14; and d) a heavy chain variable region having a CDR1 sequence comprising amino acid residues 50 to 54 of SEQ ID NO:18, a CDR2 sequence comprising amino acid residues 69 to 85 of SEQ ID NO:18, and a CDR3 sequence comprising amino acid residues 118 to 128 of SEQ ID NO:18.

Additional preferred embodiments of the antibody or binding fragment thereof of the invention are: 1) an antibody or binding fragment thereof which comprises a light chain CDR1 sequence comprising amino acid residues 43 to 58 of SEQ ID NO:3, a light chain CDR2 sequence comprising amino acid residues 74 to 80 of SEQ ID NO:3, a light chain CDR3 sequence comprising amino acid residues 113 to 121 of SEQ ID NO:3, a heavy chain CDR1 sequence comprising amino acid residues 50 to 54 of SEQ ID NO:4, a heavy chain CDR2 sequence comprising amino acid residues 70 to 84 of SEQ ID NO:4, and a heavy chain CDR3 sequence comprising amino acid residues 117 to 126 of SEQ ID NO:4; 2) an antibody or binding fragment thereof which comprises a light chain CDR1 sequence comprising amino acid residues 43 to 58 of SEQ TD NO:8, a light chain CDR2 sequence comprising amino acid residues 74 to 80 of SEQ ID NO:8, a light chain CDR3 sequence comprising amino acid residues 113 to 121 of SEQ ID NO:8, a heavy chain CDR1 sequence comprising amino acid residues 49 to 54 of SEQ ID NO:10, a heavy chain CDR2 sequence comprising amino acid residues 69 to 84 of SEQ ID NO:10, and a heavy chain CDR3 sequence comprising amino acid residues 117 to 119 of SEQ ID NO:10; 3) an antibody or binding fragment thereof which comprises a light chain CDR1 sequence comprising amino acid residues 46 to 56 of SEQ ID NO:9, a light chain CDR2 sequence comprising amino acid residues 72 to 78 of SEQ ID NO:9, a light chain CDR3 sequence comprising amino acid residues 111 to 119 of SEQ ID NO:9, a heavy chain CDR1 sequence comprising amino acid residues 49 to 54 of SEQ ID NO:10, a heavy chain CDR2 sequence comprising amino acid residues 69 to 84 of SEQ ID NO:10, and a heavy chain CDR3 sequence comprising amino acid residues 117 to 119 of SEQ ID NO:10; 4) an antibody or binding fragment thereof which comprises a light chain CDR1 sequence comprising amino acid residues 43 to 58 of SEQ ID NO:13, a light chain CDR2 sequence comprising amino acid residues 74 to 80 of SEQ ID NO:13, a light chain CDR3 sequence comprising amino acid residues 113 to 121 of SEQ ID NO:13, a heavy chain CDR1 sequence comprising amino acid residues 50 to 54 of SEQ ID NO:14, a heavy chain CDR2 sequence comprising amino acid residues 70 to 85 of SEQ ID NO:14, and a heavy chain CDR3 sequence comprising amino acid residues 118 to 129 of SEQ ID NO:14; and 5) an antibody or binding fragment thereof which comprises a light chain CDR1 sequence comprising amino acid residues 46 to 55 of SEQ ID NO:17, a light chain CDR2 sequence comprising amino acid residues 71 to 77 of SEQ ID NO:17, a light chain CDR3 sequence comprising amino acid residues 110 to 118 of SEQ ID NO:17, a heavy chain CDR1 sequence comprising amino acid residues 50 to 54 of SEQ ID NO:18, a heavy chain CDR2 sequence comprising amino acid residues 69 to 85 of SEQ ID NO:18, and a heavy chain CDR3 sequence comprising amino acid residues 118 to 128 of SEQ ID NO:18.

An additional preferred embodiment of the antibody or binding fragment thereof of the invention is an antibody or binding fragment thereof that comprises a light chain CDR1 sequence comprising amino acid residues 44 to 54 of SEQ ID NO:3, a light chain CDR2 sequence comprising amino acid residues 70 to 76 of SEQ ID NO:3, a light chain CDR3 sequence comprising amino acid residues 109 to 117 of SEQ ID NO:3, a heavy chain CDR1 sequence comprising amino acid residues 50 to 54 of SEQ ID NO:4, a heavy chain CDR2 sequence comprising amino acid residues 69 to 85 of SEQ ID NO:4, and a heavy chain CDR3 sequence comprising amino acid residues 118 to 128 of SEQ ID NO:4.

Another preferred embodiment of the antibody or binding fragment thereof of the invention is an antibody or binding fragment thereof that comprises a light chain CDR1 sequence comprising amino acid residues 43 to 58 of SEQ ID NO:8, a light chain CDR2 sequence comprising amino acid residues 74 to 80 of SEQ ID NO:8, a light chain CDR3 sequence comprising amino acid residues 113 to 121 of SEQ ID NO:8, a heavy chain CDR1 sequence comprising amino acid residues 49 to 54 of SEQ ID NO:10, a heavy chain CDR2 sequence comprising amino acid residues 69 to 84 of SEQ ID NO:10, and a heavy chain CDR3 sequence comprising amino acid residues 117 to 119 of SEQ ID NO:10.

A further preferred embodiment of the antibody or binding fragment thereof of the invention is an antibody or binding fragment thereof that comprises a light chain CDR1 sequence comprising amino acid residues 46 to 56 of SEQ 1D NO:9, a light chain CDR2 sequence comprising amino acid residues 72 to 78 of SEQ ID NO:9, a light chain CDR3 sequence comprising amino acid residues 111 to 119 of SEQ ID NO:9, a heavy chain CDR1 sequence comprising amino acid residues 49 to 54 of SEQ ID NO:10, a heavy chain CDR2 sequence comprising amino acid residues 69 to 84 of SEQ ID NO:10, and a heavy chain CDR3 sequence comprising amino acid residues 117 to 119 of SEQ ID NO:10.

Another preferred embodiment of the antibody or binding fragment thereof of the subject invention is an antibody or binding fragment thereof that comprises a light chain CDR1 sequence comprising amino acid residues 43 to 58 of SEQ ID NO:13, a light chain CDR2 sequence comprising amino acid residues 74 to 80 of SEQ ID NO:13, a light chain CDR3 sequence comprising amino acid residues 113 to 121 of SEQ ID NO:13, a heavy chain CDR1 sequence comprising amino acid residues 50 to 54 of SEQ ID NO:14, a heavy chain CDR2 sequence comprising amino acid residues 69 to 85 of SEQ ID NO:14, and a heavy chain CDR3 sequence comprising amino acid residues 118 to 129 of SEQ ID NO:14.

Another preferred embodiment of the antibody or binding fragment thereof of the subject invention is an antibody or binding fragment thereof which comprises a light chain CDR1 sequence comprising amino acid residues 46 to 55 of SEQ ID NO:17, a light chain CDR2 sequence comprising amino acid residues 71 to 77 of SEQ ID NO:17, a light chain CDR3 sequence comprising amino acid residues 110 to 118 of SEQ ID NO:17, a heavy chain CDR1 sequence comprising amino acid residues 50 to 54 of SEQ ID NO:18, a heavy chain CDR2 sequence comprising amino acid residues 69 to 85 of SEQ ID NO:18, and a heavy chain CDR3 sequence comprising amino acid residues 118 to 128 of SEQ ID NO:18.

Further details of the antibodies or binding fragments thereof of the invention are provided in the section below entitled "Antibodies".

The subject invention further provides an assay kit comprising the antibody or binding fragment thereof, as well as an assay device comprising the antibody or binding fragment thereof. Preferably, the assay device is a lateral flow assay device. Further details of the assay kits and assay devices are provided below in the section entitled "Assay Kits and Devices".

The invention further provides a method of detecting quetiapine in a sample. The method comprises: (i) contacting a sample with an antibody or binding fragment thereof according to the subject invention which is labeled with a detectable marker, wherein the labeled antibody or binding fragment thereof and quetiapine present in the sample form a labeled complex; and (ii) detecting the labeled complex so as to detect quetiapine in the sample. Further details of the method of detecting quetiapine in accordance with the invention are provided in the section below entitled "Immunoassays".

Further provided is a competitive immunoassay method for detecting quetiapine in a sample. The method comprises: (i) contacting a sample with an antibody or binding fragment thereof according to the subject invention, and with quetiapine or a competitive binding partner of quetiapine, wherein one of the antibody or binding fragment thereof and the quetiapine or competitive binding partner thereof is labeled with a detectable marker, and wherein sample quetiapine competes with the quetiapine or competitive binding partner thereof for binding to the antibody or binding fragment thereof; and (ii) detecting the label so as to detect sample quetiapine. Further details of the competitive immunoassay method of detecting quetiapine in accordance with the subject invention are provided in the section below entitled "Immunoassays".

In a preferred embodiment of the subject invention, the detection of quetiapine is accompanied by the detection of one or more analytes in addition to quetiapine. Preferably the one or more analytes are anti-psychotic drugs other than quetiapine, and more preferably the anti-psychotic drugs other than quetiapine are selected from the group consisting of: aripiprazole, risperidone, paliperidone, olanzapine, and metabolites thereof.

As discussed above, the antibodies or binding fragment thereof of the subject invention can be used in assays to detect the presence and/or amount of the anti-psychotic drug in patient samples. Such detection permits therapeutic drug monitoring enabling all of the benefits thereof. Detection of levels of anti-psychotic drugs may be useful for many purposes, each of which represents another embodiment of the subject invention, including: determination of patient adherence or compliance with prescribed therapy; use as a decision tool to determine whether a patient should be converted from an oral anti-psychotic regimen to a long-acting injectable anti-psychotic regimen; use as a decision tool to determine if the dose level or dosing interval of oral or injectable anti-psychotics should be increased or decreased to ensure attainment or maintenance of efficacious or safe drug levels; use as an aid in the initiation of anti-psychotic drug therapy by providing evidence of the attainment of minimum pK levels; use to determine bioequivalence of anti-psychotic drug in multiple formulations or from multiple sources; use to assess the impact of polypharmacy and potential drug-drug interactions; and use as an indication that a patient should be excluded from or included in a clinical trial and as an aid in the subsequent monitoring of adherence to clinical trial medication requirements.

Antibodies

The present invention provides an isolated antibody or binding fragment thereof which binds to quetiapine. The term "antibody" refers to a specific protein capable of binding an antigen or portion thereof (in accordance with this invention, capable of binding to an anti-psychotic drug or metabolite thereof). An antibody is produced in response to an immunogen which may have been introduced into a host, e.g., an animal or a human, by injection. The generic term "antibody" includes polyclonal antibodies, monoclonal antibodies, and antibody fragments.

"Antibody" or "antigen-binding antibody fragment" refers to an intact antibody, or a fragment thereof, that competes with the intact antibody for binding. Generally speaking, an antibody or antigen-binding antibody fragment, is said to specifically bind an antigen when the dissociation constant is less than or equal to 1 µM, preferably less than or equal to 100 nM and most preferably less than or equal to 10 nM. Binding can be measured by methods know to those skilled in the art, an example being the use of a BIAcore™ instrument.

Antibodies are made up of two heavy chains and two light chains. Each heavy chain has one variable domain or region ($V_H$) followed by a constant domain or region ($C_H1$), a hinge region, and two more constant domains or regions ($C_H2$ and $C_H3$). Each light chain has one variable domain or region ($V_L$) and one constant domain or region (CO. The variable domains or regions of the heavy and light chains form the paratope of the antibody (a structure analogous to a lock), which is specific for a particular epitope (similarly analogous to a key), allowing the paratope and the epitope to bind together with precision. Within the variable domain, variable loops of β-strands, three each on the light and heavy chains, are responsible for binding to the antigen. These loops arc referred to as the complementarity determining regions (CDRs, namely CDR1, CDR2, and CDR3).

Antibody fragments comprise a portion of an intact antibody, preferably the antigen binding or variable region of the intact antibody. Binding fragments include Fab, Fab', $F(ab')_2$, and Fv fragments; diabodies; minibodies; linear antibodies; single-chain antibody molecules (e.g., scFV); and multispecific antibodies formed from antibody fragments. An antibody other than a "bispecific" or "bifunctional" antibody is understood to have each of its binding sites identical.

As used herein, "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. Two antibodies are said to "bind the same epitope" ("compete") if one antibody is shown to compete with the second antibody in a competitive binding assay, by any of the methods well known to those skilled in the art (such as the BIAcore™ method referred to above). In reference to a hapten (such as quetiapine or other antipsychotic drug), an antibody can be generated against the non-antigenic hapten molecule by conjugating the hapten to an immunogenic carrier. An antibody is then generated which recognizes an "epitope" defined by the hapten.

"Isolated" when used in the context of an antibody means altered "by the hand of man" from any natural state; i.e., that, if it occurs in nature, it has been changed or removed from its original environment, or both. For example, a naturally occurring antibody naturally present in a living animal in its natural state is not "isolated", but the same antibody separated from the coexisting materials of its natural state is "isolated", as the term is employed herein. Antibodies may occur in a composition, such as an immunoassay reagent, which are not naturally occurring compositions, and therein remain isolated antibodies within the meaning of that term as it is employed herein.

"Cross-reactivity" refers to the reaction of an antibody with an antigen that was not used to induce that antibody.

The term "conjugate" refers to any substance formed from the joining together of separate parts. Representative conjugates include those formed by the joining together of a small molecule and a large molecule, such as a carrier or a polyamine polymer, particularly a protein. In the conjugate the small molecule may be joined at one or more active sites on the large molecule.

The term "hapten" refers to a partial or incomplete antigen. A hapten is a protein-free substance, which is not capable of stimulating antibody formation, but which does react with antibodies. The antibodies are formed by coupling a hapten to a high molecular weight immunogenic carrier, and then injecting this coupled product, i.e., an immunogen, into a human or animal subject.

The term "immunogen" refers to a substance capable of eliciting, producing, or generating an immune response in an organism.

An "immunogenic carrier," as used herein, is an immunogenic substance that can join at one or more positions with haptens, thereby enabling the production of antibodies that can bind with these haptens. Examples of immunogenic carrier substances include, but are not limited to, proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Preferably, the antibody or binding fragment thereof of the subject invention will bind to the drug and any desired pharmacologically active metabolites. By altering the location of the attachment of an immunogenic carrier in a drug conjugate, selectivity and cross-reactivity with metabolites and/or related drugs can be engineered into the antibodies. For quetiapine, cross-reactivity with quetiapine metabolites such as N-desalkylquetiapine (norquetiapine), quatiapine sulfoxide, O-desalkylquetiapine or 7-hydroxy quetiapine may or may not be desirable. Antibodies may be generated that detect multiple ones of these drugs and/or metabolites, or antibodies may be generated that detect each separately (thus defining the antibody "specific binding" properties). An antibody specifically binds one or more compounds when its binding of the one or more compounds is equimolar or substantially equimolar.

The antibodies or binding fragments thereof herein are described by the nucleotide and amino acid sequences of their variable domains. Each was generated by inoculating a host with a conjugate comprising an anti-psychotic drug conjugated to an immunogenic carrier. Having now provided the nucleotide and amino acid sequences thereof, the antibodies can be produced by the recombinant methods such as are described in U.S. Pat. No. 4,166,452.

Antibody fragments which contain specific binding sites for the anti-psychotic drug may also be generated. Such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse et al., *Science* 256:1270-1281 (1989)). Fab, Fv and ScFv antibody fragments can all be expressed in and secreted from *Escherichia coli*, allowing for the production of large amounts of these fragments. Alternatively, Fab'-SH fragments can be directly recovered from *E. coli* and chemically coupled to form F(ab')2 fragments (Carter et al., *BioTechnology* 10:163-167 (1992)). Other techniques for the production of antibody fragments are known to those skilled in the art. Single chain Fv fragments (scFv) are also envisioned (see U.S. Pat. Nos. 5,761,894 and 5,587,458). Fv and sFv fragments are the only species with intact combining sites that are devoid of constant regions; thus, they are likely to show reduced non-specific binding. The antibody fragment may also be a "linear antibody" e.g., as described in U.S. Pat. No. 5,642,870, for example. Such linear antibody fragments may be monospecific or bispecific.

Assay Kits and Devices

An assay kit (also referred to as a reagent kit) can also be provided comprising an antibody or binding fragment thereof as described above. A representative reagent kit may comprise an antibody or binding fragment thereof that binds to the anti-psychotic drug, quetiapine, a complex comprising an analog of an anti-psychotic drug or a derivative thereof coupled to a labeling moiety, and may optionally also comprise one or more calibrators comprising a known amount of an anti-psychotic drug or a related standard.

The phrase "assay kit" refers to an assembly of materials and reagents that is used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. An assay kit embodying features of the present invention comprises antibodies or binding fragment thereof which bind quetiapine. The kit may further comprise competitive binding partners of quetiapine and calibration and control materials.

The phrase "calibration and control material" refers to any standard or reference material containing a known amount of an analyte. A sample suspected of containing an analyte and the corresponding calibration material are assayed under similar conditions. The concentration of analyte is calculated by comparing the results obtained for the unknown specimen with the results obtained for the standard. This is commonly done by constructing a calibration curve.

Antibodies embodying features of the present invention can be included in a kit, container, pack, or dispenser together with instructions for their utilization. When the antibodies are supplied in a kit, the different components of the immunoassay may be packaged in separate containers and admixed prior to use. Such packaging of the components separately may permit long-term storage without substantially diminishing the functioning of the active components. Furthermore, reagents can be packaged under inert environments, e.g., under a positive pressure of nitrogen gas, argon gas, or the like, which is especially preferred for reagents that are sensitive to air and/or moisture.

Reagents included in kits embodying features of the present invention can be supplied in all manner of containers such that the activities of the different components are substantially preserved while the components themselves are not substantially adsorbed or altered by the materials of the container. Suitable containers include, but are not limited to, ampules, bottles, test tubes, vials, flasks, syringes, envelopes, e.g., foil-lined, and the like. The containers may be comprised of any suitable material including, but not limited to, glass, organic polymers, e.g., polycarbonate, polystyrene, polyethylene, etc., ceramic, metal, e.g., aluminum, metal alloys, e.g., steel, cork, and the like. In addition, the containers may comprise one or more sterile access ports, e.g., for access via a needle, such as may be provided by a septum. Preferred materials for septa include rubber and polytetrafluoroethylene of the type sold under the trade name TEFLON by DuPont (Wilmington, Del.). In addition, the containers may comprise two or more compartments separated by partitions or membranes that can be removed to allow mixing of the components.

Reagent kits embodying features of the present invention may also be supplied with instructional materials. Instructions may be printed, e.g., on paper and/or supplied in an electronically-readable medium. Alternatively, instructions may be provided by directing a user to an internet website, e.g., specified by the manufacturer or distributor of the kit and/or via electronic mail.

The antibody or binding fragment thereof may also be provided as part of an assay device. Such assay devices include lateral flow assay devices. A common type of disposable lateral flow assay device includes a zone or area for receiving the liquid sample, a conjugate zone, and a reaction zone. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120,643, and 6,228,660 all of which are incorporated herein by reference in their entireties.

Another type of assay device is a non-porous assay device having projections to induce capillary flow. Examples of such assay devices include the open lateral flow device as disclosed in PCT International Publication Nos. WO 2003/103835, WO 2005/089082, WO 2005/118139, and WO 2006/137785, all of which are incorporated herein by reference in their entireties.

In a non-porous assay device, the assay device generally has at least one sample addition zone, at least one conjugate zone, at least one reaction zone, and at least one wicking zone. The zones form a flow path by which sample flows from the sample addition zone to the wicking zone. Also included are capture elements, such as antibodies, in the reaction zone, capable of binding to the analyte, optionally deposited on the device (such as by coating); and a labeled conjugate material also capable of participating in reactions that will enable determination of the concentration of the analyte, deposited on the device in the conjugate zone, wherein the labeled conjugate material carries a label for detection in the reaction zone. The conjugate material is dissolved as the sample flows through the conjugate zone forming a conjugate plume of dissolved labeled conjugate material and sample that flows downstream to the reaction zone. As the conjugate plume flows into the reaction zone, the conjugated material will be captured by the capture elements such as via a complex of conjugated material and analyte (as in a "sandwich" assay) or directly (as in a "competitive" assay). Unbound dissolved conjugate material will be swept past the reaction zone into the at least one wicking zone. Such devices can include projections or micropillars in the flow path.

An instrument such as that disclosed in US Patent Publication Nos. US20060289787A1 and US 20070231883A1, and U.S. Pat. Nos. 7,416,700 and 6,139,800, all of which are incorporated herein by reference in their entireties, is able to detect the bound conjugated material in the reaction zone. Common labels include fluorescent dyes that can be detected by instruments which excite the fluorescent dyes and incorporate a detector capable of detecting the fluorescent dyes.

Immunoassays

The antibodies or binding fragment thereof thus produced can be used in immunoassays to recognize/bind to the anti-psychotic drug, thereby detecting the presence and/or amount of the drug in a patient sample. Preferably, the assay format is a competitive immunoassay format. Such an assay format and other assays are described, among other places, in Hampton et al. (*Serological Methods, A Laboratory Manual*, APS Press, St. Paul, Minn. 1990) and Maddox et al. (*J. Exp. Med.* 158:12111, 1983).

The term "analyte" refers to any substance or group of substances, the presence or amount of which is to be determined. Representative anti-psychotic drug analytes include, but are not limited to, risperidone, paliperidone, olanzapine, aripiprazole, and quetiapine.

The term "competitive binding partner" refers to a substance or group of substances, such as may be employed in a competitive immunoassay, which behave similarly to an analyte with respect to binding affinity to an antibody. Representative competitive binding partners include, but are not limited to, anti-psychotic drug derivatives and the like.

The term "detecting" when used with an analyte refers to any quantitative, semi-quantitative, or qualitative method as well as to all other methods for determining an analyte in general, and an anti-psychotic drug in particular. For example, a method that merely detects the presence or absence of an anti-psychotic drug in a sample lies within the scope of the present invention, as do methods that provide data as to the amount or concentration of the anti-psychotic drug in the sample. The terms "detecting", "determining", "identifying", and the like are used synonymously herein, and all lie within the scope of the present invention.

A preferred embodiment of the subject invention is a competitive immunoassay wherein antibodies or binding fragments thereof which bind the anti-psychotic drug, or the drug or competitive binding partner thereof, are attached to a solid support (such as the reaction zone in a lateral flow assay device) and labeled drug or competitive binding partner thereof, or labeled antibody, respectively, and a sample derived from the host are passed over the solid support and the amount of label detected attached to the solid support can be correlated to a quantity of drug in the sample.

Any sample that is suspected of containing an analyte, e.g., an anti-psychotic drug, can be analyzed in accordance with the methods of the presently preferred embodiments. The sample can be pretreated if desired and can be prepared in any convenient medium that does not interfere with the assay. Preferably, the sample comprises an aqueous medium such as a body fluid from a host, most preferably plasma or serum.

It is to be understood that all manner of immunoassays employing antibodies are contemplated for use in accordance with the presently preferred embodiments, including assays in which antibodies are bound to solid phases and assays in which antibodies are in liquid media. Methods of immunoassays that can be used to detect analytes using antibodies embodying features of the present invention include, but are not limited to, competitive (reagent limited) assays wherein labeled analyte (analyte analog) and analyte in a sample compete for antibodies and single-site immunometric assays wherein the antibody is labeled; and the like.

All examples were carried out using standard techniques, which are well known and routine to those of skill in the art, except where otherwise described in detail. Routine molecular biology techniques of the following examples can be carried out as described in standard laboratory manuals, such as Sambrook et al., *Molecular Cloning: A Laboratory Manual*, 2nd Ed., Cold Spring Habor Laboratory Press, Cold Spring Harbor, N.Y. (1989).

Related applications all incorporated herein by reference in their entireties include: "Haptens of Aripiprazole" (U.S. Provisional Patent Appl. No. 61/691,450, filed Aug. 21, 2012, and US 20140163206, filed Aug. 20, 2013); "Haptens of Olanzapine" (U.S. Provisional Patent Appl. No. 61/691, 454, filed Aug. 21, 2012, and US 20140213766, filed Aug. 20, 2013); "Haptens of Paliperidone" (U.S. Provisional Patent Appl. No. 61/691,459, filed Aug. 21, 2012, and US 20140213767, filed Aug. 20, 2013); "Haptens of Quetiapine" (U.S. Provisional Patent Appl. No. 61/691,462, filed Aug. 21, 2012, and US 20140221616, filed Aug. 20, 2013); "Haptens of Risperidone and Paliperidone" (U.S. Provisional Patent Appl. No. 61/691,469, filed Aug. 21, 2012, and US 20140155585, Aug. 20, 2013, now U.S. Pat. No. 9,012, 648, issued Apr. 21, 2015); "Antibodies to Aripiprazole Haptens and Use Thereof" (U.S. Provisional Patent Appl. No. 61/691,544, filed Aug. 21, 2012, and US 20140057299, filed Aug. 20, 2013); "Antibodies to Olanzapine Haptens and Use Thereof" (U.S. Provisional Patent Appl. No. 61/691,572, filed Aug. 21, 2012, and US 20140057303, filed Aug. 20, 2013); "Antibodies to Paliperidone Haptens and Use Thereof" (U.S. Provisional Patent Appl. No. 61/691, 634, filed Aug. 21, 2012, and US 20140057297, filed Aug. 20, 2013); "Antibodies to Quetiapine Haptens and Use Thereof" (U.S. Provisional Patent Appl. No. 61/691,598, filed Aug. 21, 2012, and US 20140057305, filed Aug. 20, 2013); "Antibodies to Risperidone Haptens and Use Thereof" (U.S. Provisional Patent Appl. No. 61/691,615, filed Aug. 21, 2012, and US 20140057301, filed Aug. 20, 2013); "Antibodies to Aripiprazole and Use Thereof" (U.S. Provisional Patent Appl. No. 61/691,522, filed Aug. 21, 2012, and US 20140057300, filed Aug. 20, 2013); "Antibodies to Olanzapine and Use Thereof" (U.S. Provisional Patent Appl. No. 61/691,645, filed Aug. 21, 2012, and US 20140057304, filed Aug. 20, 2013); "Antibodies to Paliperidone and Use Thereof" (U.S. Provisional Patent Appl. No. 61/691,692, filed Aug. 21, 2012, and US 20140057298, filed Aug. 20, 2013); "Antibodies to Risperidone and Use Thereof" (U.S. Provisional Patent Appl. No. 61/691,675, filed Aug. 21, 2012US 20140057302, filed Aug. 20, 2013); "Antibodies to Quetiapine and Use Thereof" (U.S. Provisional Patent Appl. No. 61/691,659, filed Aug. 21, 2012, and US 20140057306, filed Aug. 20, 2013); "Antibodies to Risperidone and Use Thereof" (U.S. Provisional Patent Appl. No. 61/790,880, filed Mar. 15, 2013); and "Antibodies to Risperidone and Use Thereof" (U.S. Provisional Patent Appl. No. 62/268,898, filed Dec. 17, 2015).

EXAMPLES

The invention can be further understood in view of the following non-limiting examples.

Example 1

Antibodies to Quetiapine

The antibodies designated 13.5 sub-clone 7C6-2, 13.5 sub-clone 7G8-A1, 13.2 clone 158, and 2H8-9 were produced by standard hybridoma methods.

Materials and Methods

Hybridoma cells were generated from immunizations with quetiapine immunogens. TRIzol® Reagent was obtained from Invitrogen/Ambion (Grand Island, N.Y.; Cat. No.: 15596-026). PrimeScript™ 1st Strand cDNA Synthesis Kit was obtained from Takara Bio/Clontech Laboratories (Mountain View, Calif.; Cat. No. 6110A). SuperScript® III 1st Strand Synthesis System was obtained from Invitrogen (Grand Island, N.Y.; Cat. No. 18080-051). DNA Marker III was obtained from Tiangen Biotech (Beijing, China; Cat. No. MD103).

Total RNA Extraction:

Total RNA was isolated from the hybridoma cells following the technical manual of TRIzol® Reagent. The total RNA was analyzed by agarose gel electrophoresis.

RT-PCR:

Total RNA was reverse transcribed into cDNA using isotype-specific anti-sense primers or universal primers following the technical manual of PrimeScript™ 1st Strand cDNA Synthesis Kit or SuperScript™ III 1st Strand Synthesis System. The antibody fragments of $V_H$ and $V_L$ were amplified according to the standard operating procedure of RACE of GenScript.

Cloning of Antibody Genes:

Amplified antibody fragments were separately cloned into a standard cloning vector using standard molecular cloning procedures.

Screening and Sequencing:

Colony PCR screening was performed to identify clones with inserts of correct sizes. No less than five single colonies with inserts of correct sizes were sequenced for each antibody fragment.

Results

Total RNA Extraction—

The isolated total RNA of the sample was run alongside a DNA marker Marker 111 on a 1.5% agarose/GelRed™ gel.

PCR Product—

Four microliters of PCR products of each sample were run alongside the DNA marker Marker III on a 1.5% agarose/GelRed™ gel. The PCR products were purified and stored at −20° C.

Example 2

Antibodies to Quetiapine

Antibody 13.5 Sub-Clone 7C6-2

The hybridoma designated 13.5 sub-clone 7C6-2 secretes a monoclonal antibody (mAb) specific for quetiapine. The antibody is designated 13.5 sub-clone 7C6-2. The nucleotide sequence of mAb 13.5 sub-clone 7C6-2's light chain variable region ($V_L$) is designated SEQ ID NO:1 and that of the heavy chain variable region ($V_H$) is designated SEQ ID NO:2. Within mAb 13.5 sub-clone 7C6-2's $V_L$, nucleotides 127-174 of SEQ ID NO:1 represent the first complementarity determining region (CDR1); nucleotides 220-240 of SEQ ID NO:1 represent the second complementarity determining region (CDR2); and nucleotides 337-363 of SEQ ID NO:1 represent the third complementarity determining region (CDR3). Within mAb 13.5 sub-clone 7C6-2's $V_H$, nucleotides 148-162 of SEQ ID NO:2 represent the CDR1; nucleotides 205-252 of SEQ ID NO:2 represent the CDR2; and nucleotides 349-378 of SEQ ID NO:2 represent the CDR3.

The corresponding predicted amino acid sequences of mAb 13.5 sub-clone 7C6-2's variable chain regions were also determined, and are designated SEQ ID NO:3 (light chain) and SEQ ID NO:4 (heavy chain). Within mAb 13.5 sub-clone 7C6-Ts $V_L$, amino acid residues 43-58 of SEQ ID NO:3 represent the CDR1; amino acid residues 74-80 of SEQ ID NO:3 represent the CDR2; and amino acid residues 113-121 of SEQ ID NO:3 represent the CDR3. Within mAb 13.5 sub-clone 7C6-2's $V_H$, amino acid residues 50-54 of SEQ ID NO:4 represent the CDR1; amino acid residues 69-84 of SEQ ID NO:4 represent the CDR2; and amino acid residues 117-126 of SEQ ID NO:4 represent the CDR3.

Antibody 13.5 Sub-Clone 7G8-A1 (First)

The hybridoma designated 13.5 sub-clone 7G8-A1 (first) secretes a monoclonal antibody specific for quetiapine. The antibody is designated 13.5 sub-clone 7G8-A1 (first). The nucleotide sequence of mAb 13.5 sub-clone 7G8-A1 (first)'s $V_L$ is designated SEQ ID NO:5 and that of the $V_H$ is designated SEQ ID NO:7. Within mAb 13.5 sub-clone 7G8-A1 (first)'s $V_L$, nucleotides 127-174 of SEQ ID NO:5 represent the CDR1; nucleotides 220-240 of SEQ ID NO:5 represent the CDR2; and nucleotides 336-364 of SEQ ID NO:5 represent the CDR3. Within mAb 13.5 sub-clone 7G8-A1 (first)'s $V_H$, nucleotides 145-162 of SEQ ID NO:7 represent the CDR1; nucleotides 205-252 of SEQ ID NO:7 represent the CDR2; and nucleotides 349-357 of SEQ ID NO:7 represent the CDR3.

The corresponding predicted amino acid sequences of mAb 13.5 sub-clone 7G8-A1 (first)'s variable chain regions were also determined, and are designated SEQ ID NO:8 (light chain) and SEQ ID NO:10 (heavy chain). Within mAb 13.5 sub-clone 7G8-A1 (first)'s $V_L$, amino acid residues 43-58 of SEQ ID NO:8 represent the CDR1; amino acid residues 74-80 of SEQ ID NO:8 represent the CDR2; and amino acid residues 113-121 of SEQ ID NO:8 represent the CDR3. Within mAb 13.2 sub-clone 7G8-A1 (first)'s $V_H$, amino acid residues 45-54 of SEQ ID NO:10 represent the CDR1; amino acid residues 69-84 of SEQ ID NO:10 represent the CDR2; and amino acid residues 117-119 of SEQ ID NO:10 represent the CDR3.

Antibody 13.5 Sub-Clone 7G8-A1 (Second)

The hybridoma designated 13.5 sub-clone 7G8-A1 (second) secretes a monoclonal antibody specific for quetiapine. The antibody is designated 13.5 sub-clone 7G8-A1 (second). The nucleotide sequence of mAb 13.5 sub-clone 7G8-A1 (second)'s $V_L$ is designated SEQ ID NO:6 and that of the $V_H$ is designated SEQ ID NO:7. Within mAb 13.5 sub-clone 7G8-A1 (second)'s $V_L$, nucleotides 136-168 of SEQ ID NO:6 represent the CDR1; nucleotides 214-234 of SEQ ID NO:6 represent the CDR2; and nucleotides 331-357 of SEQ ID NO:6 represent the CDR3. Within mAb 13.5 sub-clone 7G8-A1 (second)'s $V_H$, nucleotides 145-162 of SEQ ID NO:7 represent the CDR1; nucleotides 205-252 of SEQ ID NO:7 represent the CDR2; and nucleotides 349-357 of SEQ ID NO:7 represent the CDR3.

The corresponding predicted amino acid sequences of mAb 13.5 sub-clone 7G8-A1 (second)'s variable chain regions were also determined, and are designated SEQ ID NO:9 (light chain) and SEQ ID NO:10 (heavy chain). Within mAb 13.5 sub-clone 7G8-A1 (second)'s $V_L$, amino acid residues 46-56 of SEQ ID NO:9 represent the CDR1; amino acid residues 72-78 of SEQ ID NO:9 represent the CDR2; and amino acid residues 111-119 of SEQ ID NO:9 represent the CDR3. Within mAb 13.2 sub-clone 7G8-A1 (second)'s $V_H$, amino acid residues 49-54 of SEQ ID NO:10 represent the CDR1; amino acid residues 69-84 of SEQ ID NO:10 represent the CDR2; and amino acid residues 117-119 of SEQ ID NO:10 represent the CDR3.

Antibody 13.2 Clone 158

The hybridoma designated 13.2 clone 158 secretes a monoclonal antibody specific for quetiapine. The antibody is designated 13.2 clone 158. The nucleotide sequence of mAb 13.2 clone 158's $V_L$ is designated SEQ ID NO:11 and that of the $V_H$ is designated SEQ ID NO:12. Within mAb 13.2 clone 158's $V_L$, nucleotides 127-174 of SEQ ID NO:11 represent the CDR1; nucleotides 220-240 of SEQ ID NO:11 represent the CDR2; and nucleotides 337-363 of SEQ ID NO:11 represent the CDR3. Within mAb 13.2 clone 158's $V_H$, nucleotides 148-162 of SEQ ID NO:12 represent the CDR1; nucleotides 205-255 of SEQ ID NO:12 represent the CDR2; and nucleotides 352-386 of SEQ ID NO:12 represent the CDR3.

The corresponding predicted amino acid sequences of mAb 13.2 clone 158's variable chain regions were also determined, and are designated SEQ ID NO:13 (light chain) and SEQ ID NO:14 (heavy chain). Within mAb 13.2 clone 158's $V_L$, amino acid residues 43-58 of SEQ ID NO:13 represent the CDR1; amino acid residues 74-80 of SEQ ID NO:13 represent the CDR2; and amino acid residues 113-121 of SEQ ID NO:13 represent the CDR3. Within mAb 13.2 clone 158's $V_H$, amino acid residues 50-54 of SEQ ID NO:14 represent the CDR1; amino acid residues 69-85 of SEQ ID NO:14 represent the CDR2; and amino acid residues 118-129 of SEQ ID NO:14 represent the CDR3.

Antibody 2H8-9

The hybridoma designated 2H8-9 secretes a monoclonal antibody specific for quetiapine. The antibody is designated 2H8-9. The nucleotide sequence of mAb 2H8-9's $V_L$ is designated SEQ ID NO:15 and that of the $V_H$ is designated SEQ ID NO:16. Within mAb 2H8-9's $V_L$, nucleotides 136-165 of SEQ ID NO:15 represent the CDR1; nucleotides 211-231 of SEQ ID NO:15 represent the CDR2; and nucleotides 328-354 of SEQ ID NO:15 represent the CDR3. Within mAb 2H8-9's $V_H$, nucleotides 148-162 of SEQ ID NO:16 represent the CDR1; nucleotides 205-255 of SEQ ID NO:16 represent the CDR2; and nucleotides 352-384 of SEQ ID NO:16 represent the CDR3.

The corresponding predicted amino acid sequences of mAb 2H8-9's variable chain regions were also determined, and are designated SEQ ID NO:17 (light chain) and SEQ ID NO:18 (heavy chain). Within mAb 2H8-9's $V_L$, amino acid residues 46-55 of SEQ ID NO:17 represent the CDR1; amino acid residues 71-77 of SEQ ID NO:17 represent the CDR2; and amino acid residues 110-118 of SEQ ID NO:17 represent the CDR3. Within mAb 2H8-9's $V_H$, amino acid residues 50-54 of SEQ ID NO:18 represent the CDR1; amino acid residues 69-85 of SEQ ID NO:18 represent the CDR2; and amino acid residues 118-128 of SEQ ID NO:18 represent the CDR3.

Example 3

Competitive Immunoassays for Quetiapine and Multiplex Competitive Immunoassay for Aripiprazole, Olanzapine, Quetiapine, and Risperidone/Paliperidone Following a series of immunizations with quetiapine immunogens, such immunogens are found in applications US 2014/0221616 and US 2014/0057305 (e.g., Compound 9), mouse tail bleeds were tested for reactivity using an ELISA. Hybridoma supernatants were also tested. ELISA data shown in Tables 1 and 2 below shows reactivity of several hybridomas (fusion partner was NSO cells).

TABLE 1

| Dilution | blank | 6B11 | 6C1 | 7C6 | 7E12 | 7F11 | 7G8 | 158 | Ag = Bt-Cmpd#9 |
|---|---|---|---|---|---|---|---|---|---|
| 400 | 0.0042 | 2.8658 | 2.3324 | 3.5570 | 2.1778 | 3.4324 | 3.4927 | 3.9334 | |
| 400 | 0.0046 | 2.6940 | 2.4006 | 3.4019 | 2.0640 | 3.2091 | 3.7577 | 3.8828 | |
| 1200 | 0.0041 | 1.3364 | 1.0672 | 2.2842 | 0.8067 | 2.1062 | 2.2951 | 2.7713 | |
| 1200 | 0.0027 | 1.3444 | 0.8933 | 2.0116 | 0.8801 | 2.0692 | 2.1656 | 2.8238 | |
| 3600 | 0.0098 | 0.4795 | 0.3366 | 0.9598 | 0.2729 | 0.9278 | 1.0856 | 1.8965 | |
| 3600 | 0.0053 | 0.5089 | 0.3600 | 0.8461 | 0.3073 | 0.9828 | 1.0875 | 1.2518 | |
| 10800 | 0.0061 | 0.2003 | 0.1371 | 0.3777 | 0.1194 | 0.3415 | 0.4859 | 1.4510 | |
| 10800 | 0.0044 | 0.1921 | 0.1537 | 0.4002 | 0.1145 | 0.4142 | 0.5238 | 1.3111 | |

TABLE 2

| dilution | 1C2 | 2C1 | 2F11 | 3B8 |
|---|---|---|---|---|
| 400 | 2.3732 | 2.3464 | 2.4862 | 1.4609 |
| 1200 | 1.1263 | 1.0950 | 1.5078 | 0.5724 |
| 3600 | 0.4115 | 0.4360 | 0.1077 | 0.1883 |
| 10800 | 0.1796 | 0.1934 | 0.2903 | 0.0759 |
| 400 | 1.3327 | 3.1701 | 2.8448 | 0.0054 |
| 1200 | 0.5239 | 2.0077 | 1.4237 | 0.0043 |
| 3600 | 0.2017 | 0.7734 | 0.4729 | 0.0094 |
| 10800 | 0.0786 | 0.3688 | 0.1966 | 0.0074 |
| dilution | 3D11 | 4A2 | 5F1 | |

After clones were identified via ELISA reactivity, competition ELISAs were run to approximate affinity and cross-reactivity with similar compounds. FIGS. 1A to 1E show the ELISA cross-reactivity results from quetiapine hybridoma subclones.

Figure 2A:
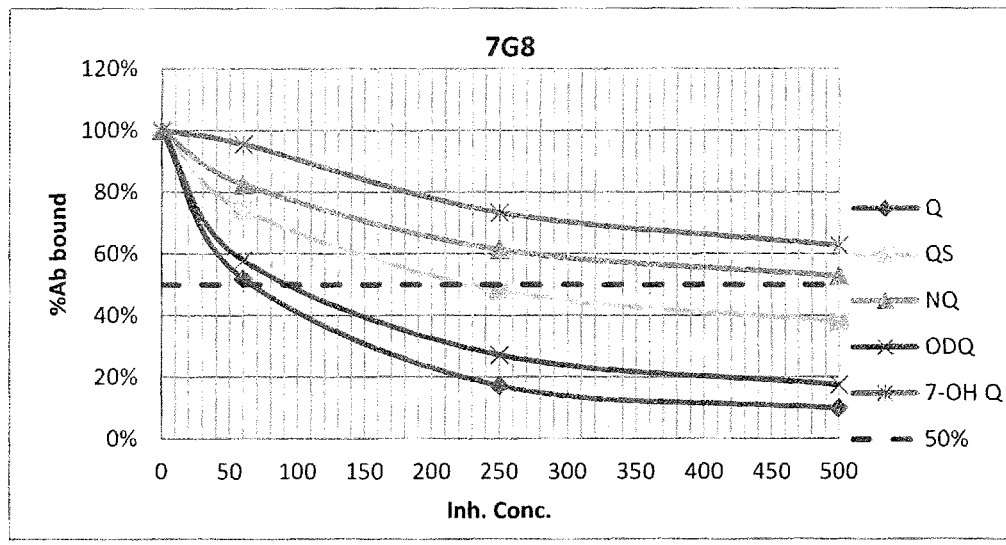
FIGS. 2A-2B show competitive ELISA results generated with various quetiapine hybridomas.
Figure 2B:
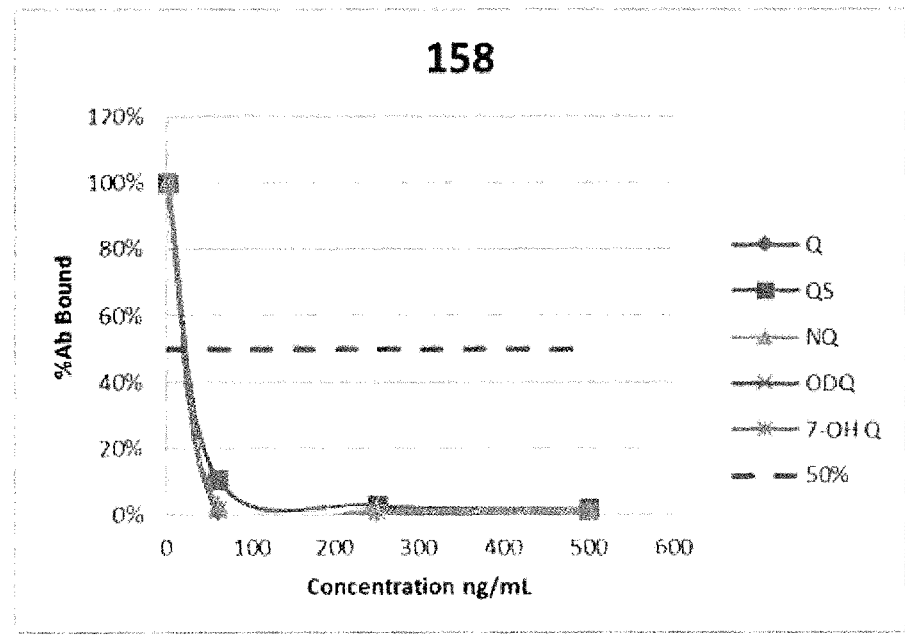

Supernatant was then tested by competition ELISA to determine if the signals were specific to quetiapine. FIGS. 2A and 2B show the results from representative hybridomas. Data shows specific reactivity to quetiapine.

Figure 3:
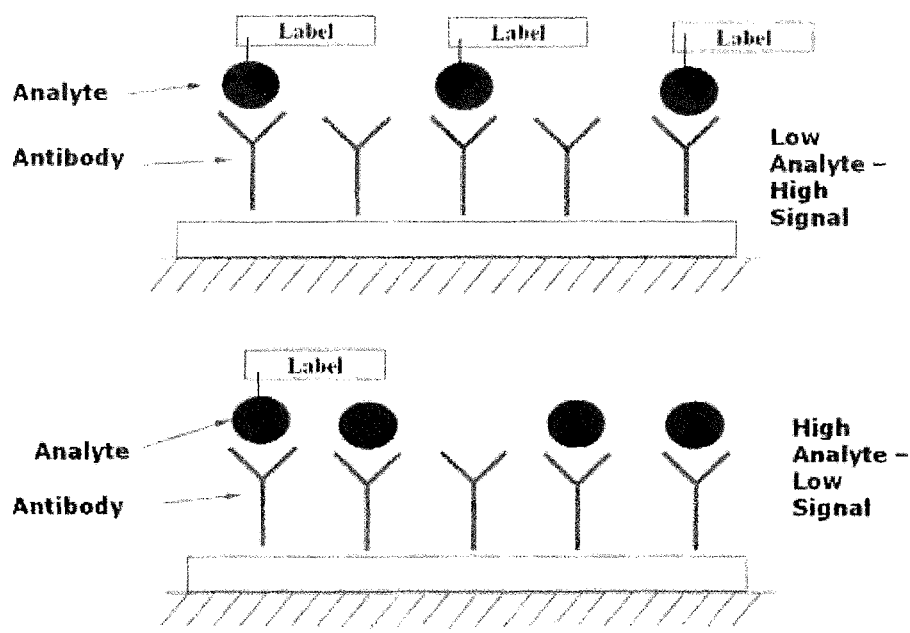
FIG. 3 shows the competitive immunoassay format used on a lateral flow assay device.
Figure 4:
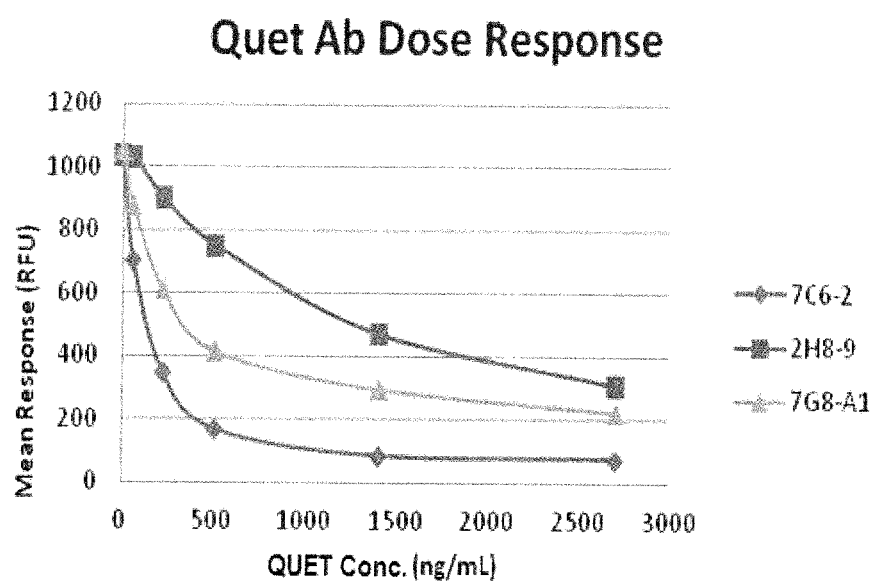
FIG. 4 shows a typical dose response curve generated with quetiapine sub-clones.

FIG. 3 shows the competitive immunoassay format used on a lateral flow assay device in which the capture antibody, a quetiapine clone, was deposited on a chip along with a detection conjugate consisting of quetiapine conjugated to a fluorophore. In this competitive format as show in FIG. 3, a low level of analyte (quetiapine) results in high signal, whereas a high level of analyte (quetiapine) results in low signal. The amount of quetiapine in the sample can be calculated from the loss of fluorescence compared to a control sample with no drug present. A typical dose response curve generated with quetiapine sub-clones is shown in FIG. 4.

Figure 5:
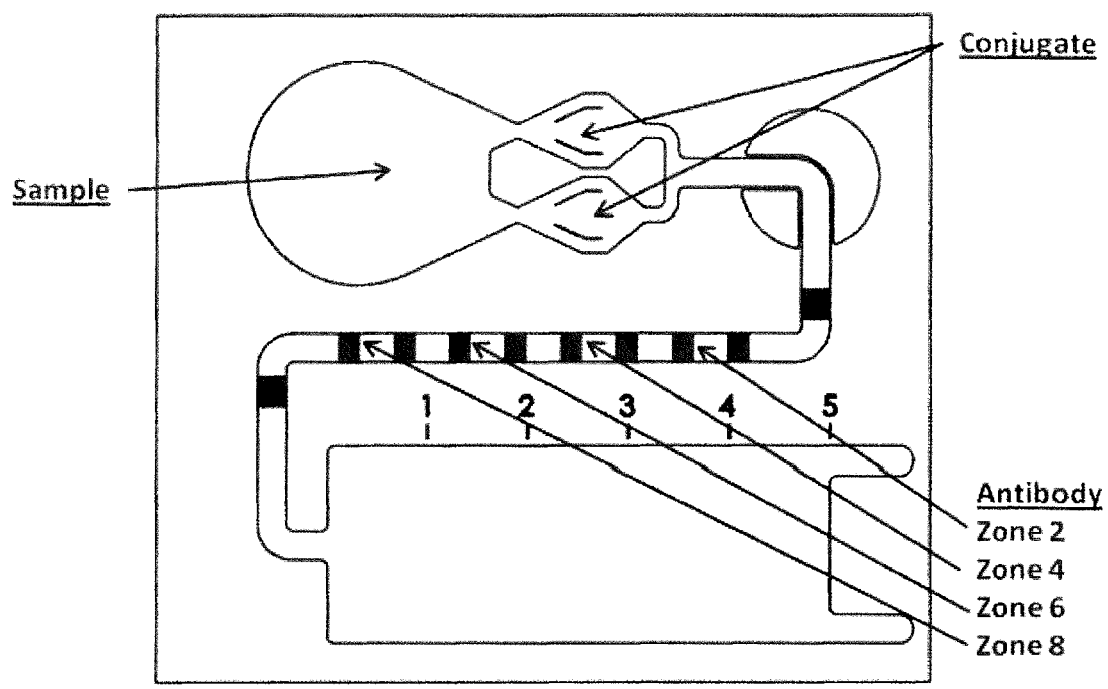
FIG. 5 shows the chip design of a lateral flow assay device according to the subject invention.
Figure 6:
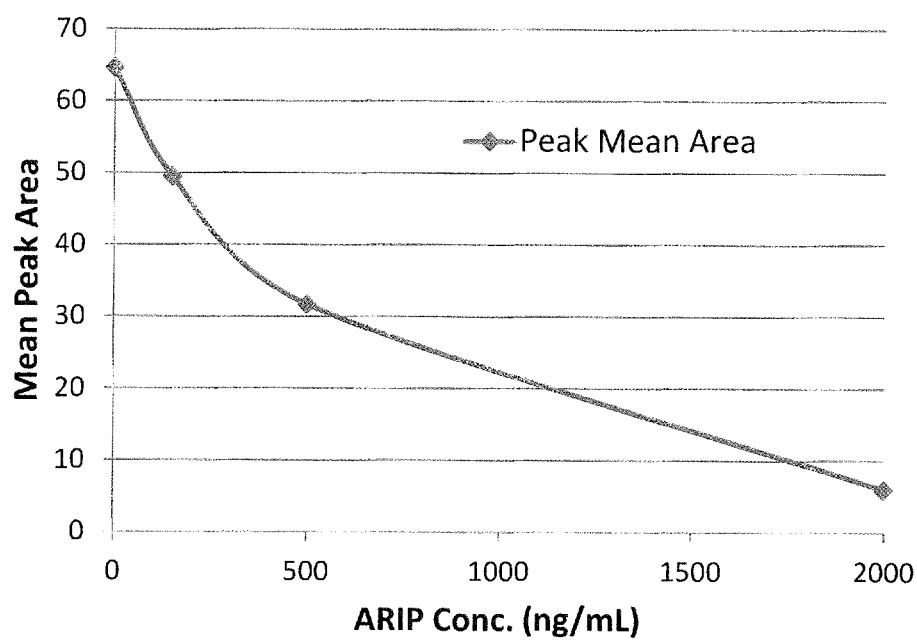
FIG. 6 shows a typical dose response curve for an aripiprazole positive control generated with antibody 5C7 and a labeled aripiprazole competitive binding partner.
Figure 7:
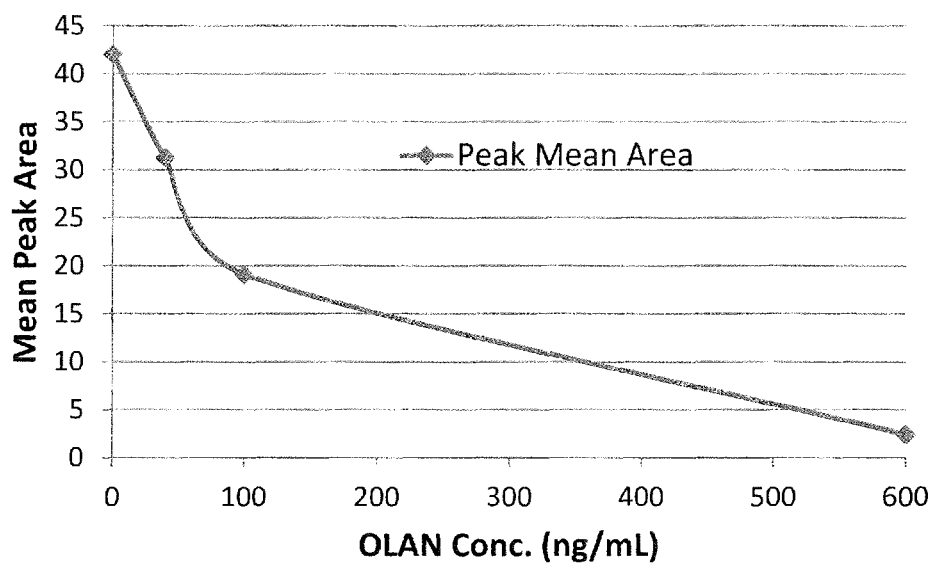
FIG. 7 shows a typical dose response curve for an olanzapine positive control generated with antibody 4G9-1 and a labeled olanzapine competitive binding partner.
Figure 8:
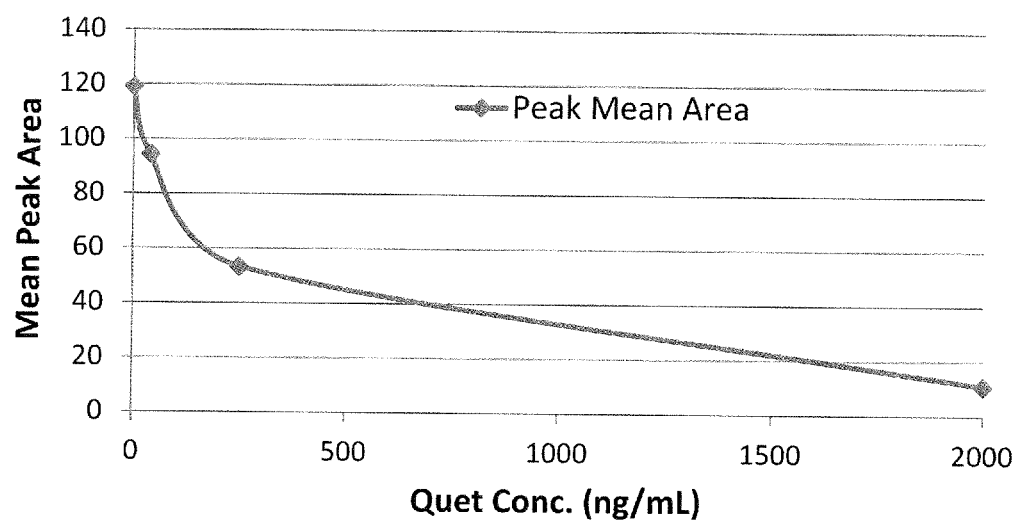
FIG. 8 shows a typical dose response curve for a quetiapine positive control generated with antibody 11 and a labeled quetiapine competitive binding partner.

FIG. 5 shows the chip design of a lateral flow assay device according to one embodiment of the subject invention. The device includes a zone or area for receiving the sample, a conjugate zone (which contains desired labeled competitive binding partner(s)), and a reaction zone (eight areas within the reaction zone are indicated; each area can contain a separate desired antibody). Sample flows from the sample zone through the conjugate zone and to the reaction zone.

Figure 9:
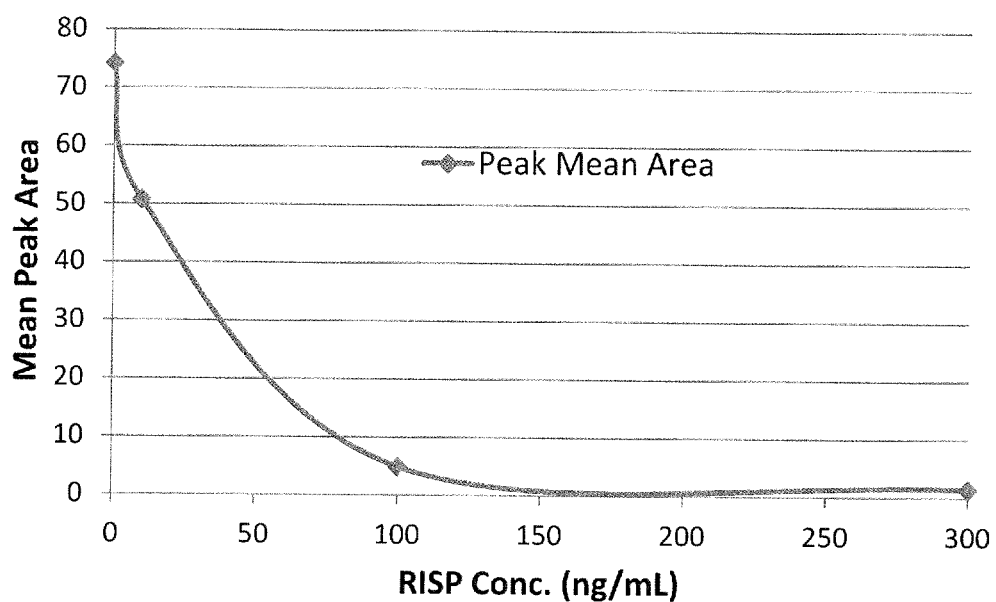
FIG. 9 shows a typical dose response curve for a risperidone positive control generated with antibody 5_9 and a labeled risperidone competitive binding partner.

FIGS. 6-9 show typical dose response curves for an aripiprazole positive control (sample containing aripiprazole) generated with antibody 5C7 deposited in reaction zone 2 and a labeled aripiprazole competitive binding partner in the conjugate zone (FIG. 6), an olanzapine positive control (sample containing olanzapine) generated with antibody 4G9-1 deposited in reaction zone 4 and a labeled olanzapine competitive binding partner in the conjugate zone (FIG. 7), a quetiapine positive control (sample containing quetiapine) generated with antibody 11 deposited in reaction zone 6 and a labeled quetiapine competitive binding partner in the conjugate zone (FIG. 8), and a risperidone positive control (sample containing risperidone) generated with antibody 5-9 deposited in reaction zone 8 and a labeled risperidone competitive binding partner in the conjugate zone (FIG. 9). The labeled competitive binding partners in the conjugate zone compete with the drugs present in the samples for binding to the antibodies. The amount of label is detected and is an indication of the amount of drug present in the sample (the amount of signal being inversely proportional to the amount of drug in the sample—see FIG. 3).

In order to confirm that conjugates of labeled competitive binding partners do not bind to antibodies deposited in the reaction zones, negative controls were conducted by using samples containing no drugs. Referring to Table 3, a sample containing no aripiprazole is deposited in the sample zone and moves by capillary action through the conjugate zone (this time containing labeled olanzapine, labeled quetiapine, and labeled risperidone, but no labeled aripiprazole) and to the reaction zone. The reaction zone again contains aripiprazole antibody (5C7) in reaction zone 2. Table 3 below shows the results, confirming that there is no dose response and the olanzapine, quetiapine, and risperidone conjugates that move by capillary action through the reaction zone do not bind to the aripiprazole antibody.

TABLE 3

Aripiprazole-Clone 5C7-Math Model 1 (0 ng/mL Conc.)

| Assay-MM | Conj | Reaction Zone | Read Position | Peak Mean Area | Peak Mean Height | Mean Background |
|---|---|---|---|---|---|---|
| ARIP-MM1 | OLAN, QUET, RISP | ARIP | 2 | 0.77 | 1.56 | 3.99 |
| ARIP-MM1 | OLAN, QUET, RISP | | 4 | −0.02 | 0.06 | 4.14 |
| ARIP-MM1 | OLAN, QUET, RISP | | 6 | 0.09 | 0.10 | 4.29 |
| ARIP-MM1 | OLAN, QUET, RISP | | 8 | 0.13 | 0.12 | 4.61 |

Other Conjugates do not bind to Aripiprazole

Referring to Table 4, a sample containing no olanzapine is deposited in the sample zone and moves by capillary action through the conjugate zone (this time containing labeled aripiprazole, labeled quetiapine, and labeled risperidone, but no labeled olanzapine) and to the reaction zone. The reaction zone again contains olanzapine antibody (4G9-1) in reaction zone 4. Table 4 below shows the results, confirming that there is no dose response and the aripiprazole, quetiapine, and risperidone conjugates that move by capillary action through the reaction zone do not bind to the olanzapine antibody.

TABLE 4

OLAN-Clone 4G9-1-Math Model 1 (0 ng/mL Conc.)

| Assay-MM | Conj | Reaction Zone | Read Position | Peak Mean Area | Peak Mean Height | Mean Background |
|---|---|---|---|---|---|---|
| OLAN-MM1 | ARIP, QUET, RISP | | 2 | −0.03 | 0.05 | 4.38 |
| OLAN-MM1 | ARIP, QUET, RISP | OLAN | 4 | 0.74 | 1.10 | 4.56 |
| OLAN-MM1 | ARIP, QUET, RISP | | 6 | 0.06 | 0.09 | 4.79 |
| OLAN-MM1 | ARIP, QUET, RISP | | 8 | 0.11 | 0.13 | 5.17 |

Other Conjugates do not bind to Olanzapine

Referring to Table 5, a sample containing no quetiapine is deposited in the sample zone and moves by capillary action through the conjugate zone (this time containing labeled aripiprazole, labeled olanzapine, and labeled risperidone, but no labeled quetiapine) and to the reaction zone. The reaction zone again contains quetiapine antibody (11) in reaction zone 6. Table 5 below shows the results, confirming that there is no dose response and the aripiprazole, olanzapine, and risperidone conjugates that move by capillary action through the reaction zone do not bind to the quetiapine antibody.

TABLE 5

Quetiapine-Clone 11-Math Model 1 (0 ng/mL Conc.)

| Assay-MM | Conj | Reaction Zone | Read Position | Peak Mean Area | Peak Mean Height | Mean Background |
|---|---|---|---|---|---|---|
| OLAN-MM1 | ARIP, OLAN, RISP | | 2 | −0.01 | 0.07 | 3.85 |
| OLAN-MM1 | ARIP, OLAN, RISP | | 4 | 0.01 | 0.12 | 4.01 |
| OLAN-MM1 | ARIP, OLAN, RISP | QUET | 6 | 0.03 | 0.08 | 4.24 |
| OLAN-MM1 | ARIP, OLAN, RISP | | 8 | 0.04 | 0.07 | 4.56 |

Other Conjugates do not bind to Quetiapine

Referring to Table 6, a sample containing no risperidone is deposited in the sample zone and moves by capillary action through the conjugate zone (this time containing labeled aripiprazole, labeled olanzapine, and labeled quetiapine, but no labeled risperidone) and to the reaction zone. The reaction zone again contains risperidone antibody (5-9) in reaction zone 8. Table 6 below shows the results, confirming that there is no dose response and the aripiprazole, olanzapine, and quetiapine conjugates that move by capillary action through the reaction zone do not bind to the risperidone antibody.

TABLE 6

Risperidone-Clone 5-9-Math Model 1 (0 ng/mL Conc.)

| Assay-MM | Conj | Reaction Zone | Read Position | Peak Mean Area | Peak Mean Height | Mean Background |
|---|---|---|---|---|---|---|
| RISP-MM1 | ARIP, OLAN, QUET | | 2 | 0.02 | 0.11 | 7.43 |
| RISP-MM1 | ARIP, OLAN, QUET | | 4 | 0.05 | 0.14 | 7.73 |

TABLE 6-continued

Risperidone-Clone 5-9-Math Model 1 (0 ng/mL Conc.)

| Assay-MM | Conj | Reaction Zone | Read Position | Peak Mean Area | Peak Mean Height | Mean Background |
|---|---|---|---|---|---|---|
| RISP-MM1 | ARIP, OLAN, QUET | | 6 | 0.20 | 0.19 | 8.11 |
| RISP-MM1 | ARIP, OLAN, QUET | RISP | 8 | 1.97 | 3.23 | 8.85 |

Other Conjugates do not bind to Risperidone

To confirm that conjugates of labeled competitive binding partners bind only to their respective antibodies deposited in the reaction zones, additional negative controls were conducted by again using samples containing no drugs. Referring to Table 7, a sample containing no aripiprazole is deposited in the sample zone and moves by capillary action through the conjugate zone (this time containing labeled aripiprazole) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. Table 7 below shows the results, confirming that there is no dose response except to the aripiprazole antibody 5C7 (in reaction zone 2).

TABLE 7

Aripiprazole-Clone 5C7-Math Model 1 (0 ng/mL Conc.)

| Assay-MM | Conj | Reaction Zone | Read Position | Peak Mean Area | Peak Mean Height | Mean Background |
|---|---|---|---|---|---|---|
| ARIP-MM1 | ARIP, OLAN, QUET, RISP | ARIP | 2 | 60.34 | 97.53 | 5.44 |
| ARIP-MM1 | ARIP, OTAN, QUET, RISP | | 4 | 2.86 | 3.91 | 11.66 |
| ARIP-MM1 | ARIP, OLAN, QUET, RISP | | 6 | 1.12 | 1.23 | 11.03 |
| ARIP-MM1 | ARIP, OLAN, QUET, RISP | | 8 | 3.14 | 4.19 | 12.94 |

Only the Aripiprazole Reaction Zone is binding

Referring to Table 8, a sample containing no olanzapine is deposited in the sample zone and moves by capillary action through the conjugate zone (this time containing labeled olanzapine) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. Table 8 below shows the results, confirming that there is no dose response except to the olanzapine antibody 4G9-1 (in reaction zone 4).

TABLE 8

OLAN-Clone 4G9-1-Math Model 1 (0 ng/mL Conc.)

| Assay-MM | Conj | Reaction Zone | Read Position | Peak Mean Area | Peak Mean Height | Mean Background |
|---|---|---|---|---|---|---|
| OLAN-MM1 | ARIP, OLAN, QUET, RISP | | 2 | 0.02 | 0.08 | 4.86 |
| OLAN-MM1 | ARIP, OLAN, QUET, RISP | OLAN | 4 | 34.23 | 51.80 | 5.39 |
| OLAN-MM1 | ARIP, OLAN, QUET, RISP | | 6 | 0.22 | 0.32 | 5.39 |
| OLAN-MM1 | ARIP, OLAN, QUET, RISP | | 8 | 0.15 | 0.17 | 5.59 |

Only the Olanzapine Reaction Zone is binding

Referring to Table 9, a sample containing no quetiapine is deposited in the sample zone and moves by capillary action through the conjugate zone (this time containing labeled quetiapine) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. Table 9 below shows the results, confirming that there is no dose response except to the quetiapine antibody 11 (in reaction zone 6).

TABLE 9

Quetiapine-Clone 11-Math Model 1 (0 ng/mL Conc.)

| Assay-MM | Conj | Reaction Zone | Read Position | Peak Mean Area | Peak Mean Height | Mean Background |
|---|---|---|---|---|---|---|
| QUET-MM1 | ARIP, OLAN, QUET, RISP | | 2 | 0.13 | 0.41 | 10.02 |
| QUET-MM1 | ARIP, OLAN, QUET, RISP | | 4 | 0.08 | 0.23 | 10.47 |
| QUET-MM1 | ARIP, OLAN, QUET, RISP | QUET | 6 | 140.35 | 181.33 | 7.91 |
| QUET-MM1 | ARIP, OLAN, QUET, RISP | | 8 | 1.58 | 2.61 | 11.53 |

Only the Quetiapine Reaction Zone is binding

Referring to Table 10, a sample containing no risperidone is deposited in the sample zone and moves by capillary action through the conjugate zone (this time containing labeled risperidone) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. Table 10 below shows the results, confirming that there is no dose response except to the risperidone antibody 5-9 (in reaction zone 8).

TABLE 10

Risperidone-Clone 5-9-Math Model 1 (0 ng/mL Conc.)

| Assay-MM | Conj | Reaction Zone | Read Position | Peak Mean Area | Peak Mean Height | Mean Background |
|---|---|---|---|---|---|---|
| RISP-MM1 | ARIP, OLAN, QUET, RISP | | 2 | 1.03 | 1.51 | 9.07 |
| RISP-MM1 | ARIP, OLAN, QUET, RISP | | 4 | 0.65 | 0.91 | 9.60 |
| RISP-MM1 | ARIP, OLAN, QUET, RISP | | 6 | 2.61 | 6.39 | 10.48 |
| RISP-MM1 | ARIP, OLAN, QUET, RISP | RISP | 8 | 55.98 | 100.91 | 11.58 |

Only the Risperidone Reaction Zone is binding

The results shown above confirm that conjugates of labeled competitive binding partners bind only to their respective antibodies in the reaction zone.

Figure 10:
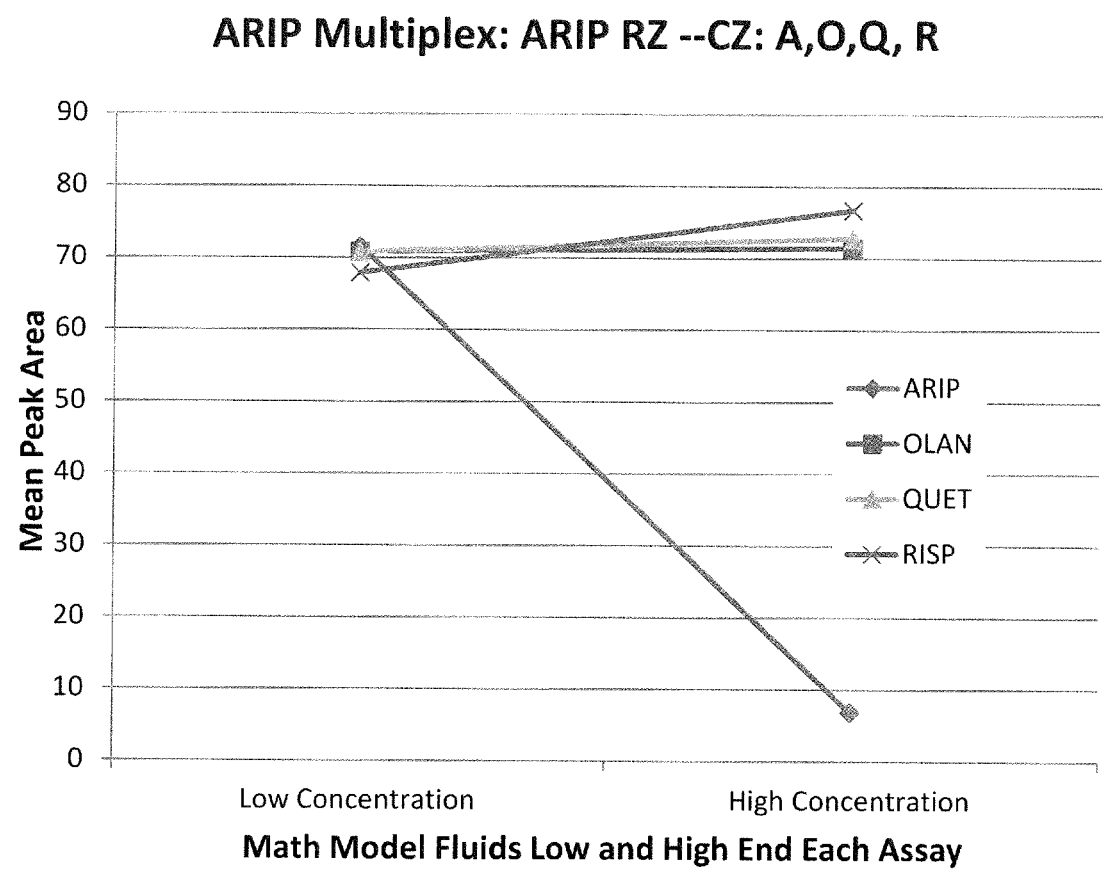
FIG. 10 shows a typical dose response curve for a sample containing aripiprazole generated with aripiprazole antibody 5C7 in the presence of labeled aripiprazole competitive binding partner, with no dose response curve for olanzapine, quetiapine, or risperidone in the presence of a labeled competitive binding partner for each.

FIGS. 10-13 show typical dose response curves in specific antibody reaction zones, and proof of dose response low/high concentration for each specific assay in the presence of other conjugates. In FIG. 10, a sample containing aripiprazole is deposited in the sample zone and moves by capillary action through the conjugate zone (this time containing labeled aripiprazole, labeled olanzapine, labeled quetiapine, and labeled risperidone) and to the reaction zone. The reaction zone again contains aripiprazole antibody (5C7) in reaction zone 2. A typical dose response curve was generated as is shown in FIG. 10 only for aripiprazole, and not for olanzapine, quetiapine, or risperidone.

Figure 11:
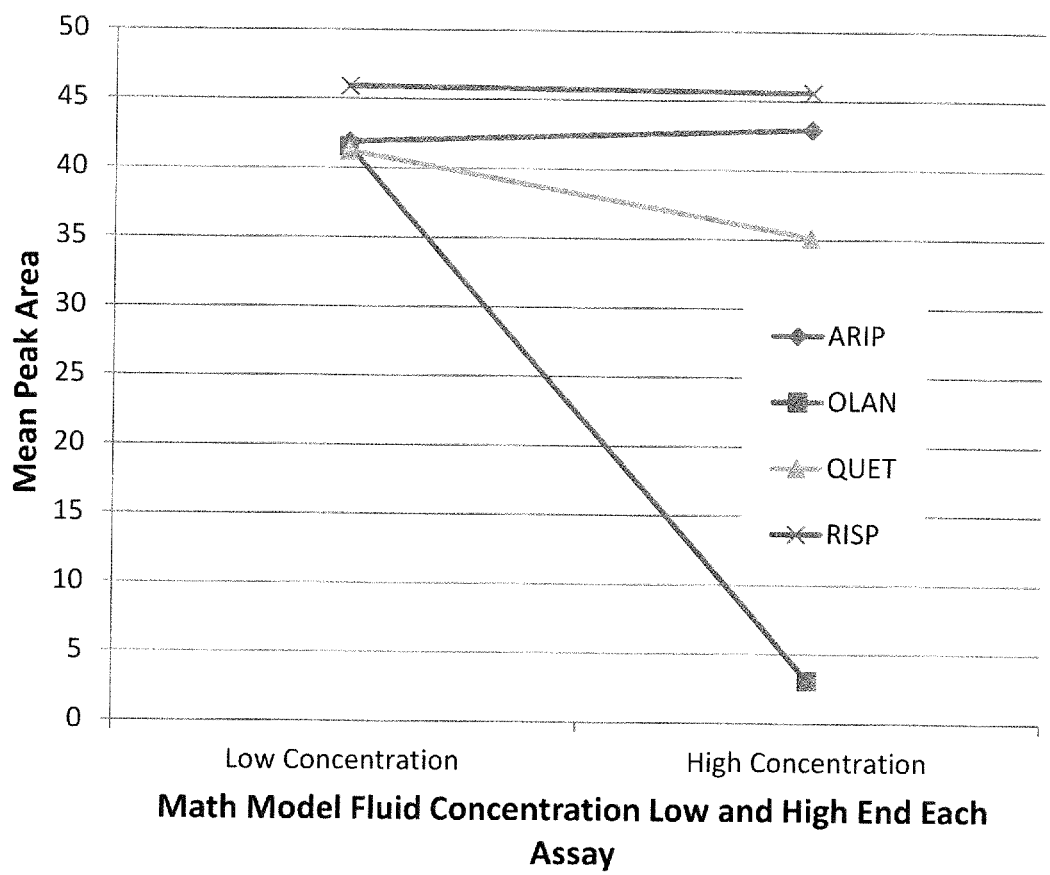
FIG. 11 shows a typical dose response curve for a sample containing olanzapine generated with olanzapine antibody 4G9-1 in the presence of a labeled olanzapine competitive binding partner, with no dose response curve for aripiprazole, quetiapine, or risperidone in the presence of a labeled competitive binding partner for each.

In FIG. 11, a sample containing olanzapine is deposited in the sample zone and moves by capillary action through the conjugate zone (this time containing labeled aripiprazole, labeled olanzapine, labeled quetiapine, and labeled risperidone) and to the reaction zone. The reaction zone again contains olanzapine antibody (4G9-1) in reaction zone 4. A typical dose response curve was generated as is shown in FIG. 11 only for olanzapine, and not for aripiprazole, quetiapine, or risperidone.

Figure 12:
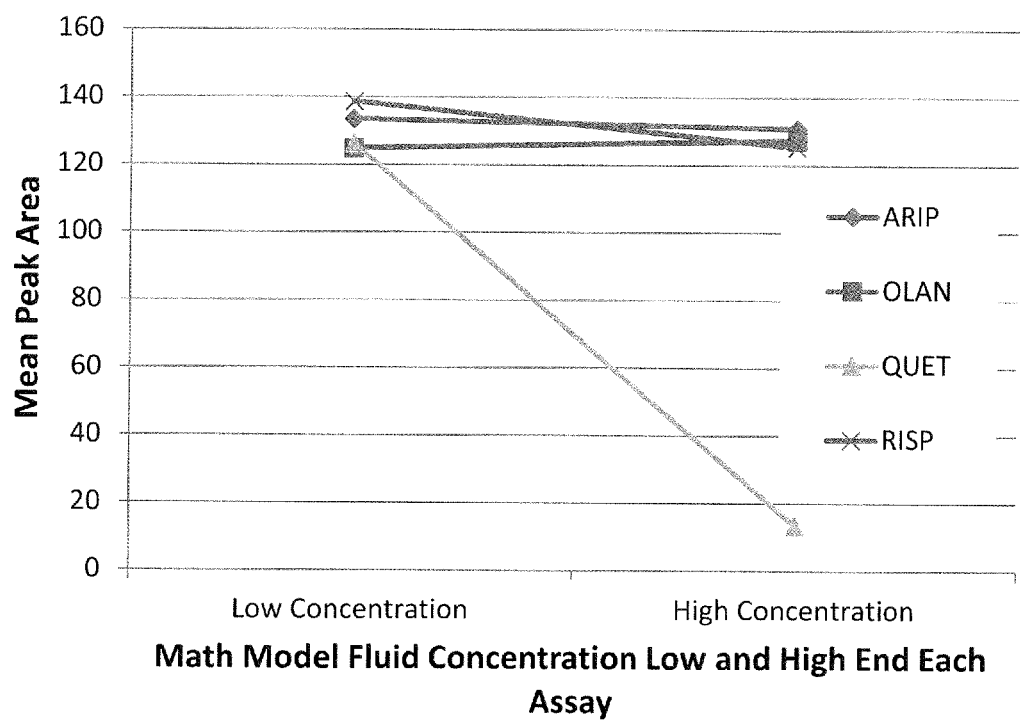
FIG. 12 shows a typical dose response curve for a sample containing quetiapine generated with quetiapine antibody 11 in the presence of a labeled quetiapine competitive binding partner, with no dose response curve for aripiprazole, olanzapine, or risperidone in the presence of a labeled competitive binding partner for each.

In FIG. 12, a sample containing quetiapine is deposited in the sample zone and moves by capillary action through the conjugate zone (this time containing labeled aripiprazole, labeled olanzapine, labeled quetiapine, and labeled risperidone) and to the reaction zone. The reaction zone again contains quetiapine antibody (11) in reaction zone 6. A typical dose response curve was generated as is shown in FIG. 12 only for quetiapine, and not for aripiprazole, olanzapine, or risperidone.

Figure 13:
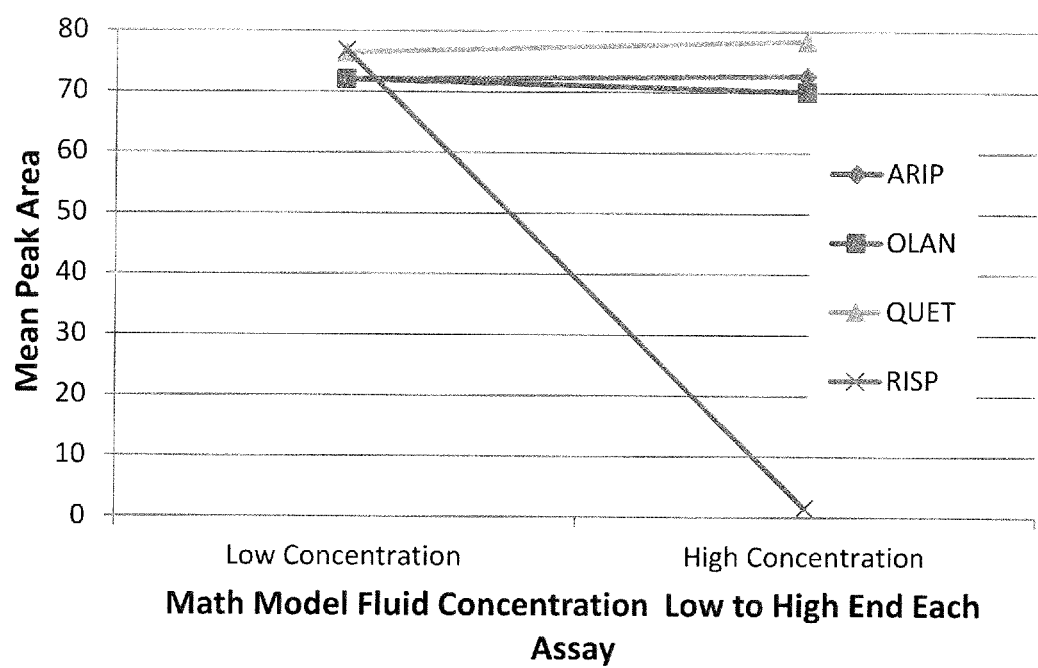
FIG. 13 shows a typical dose response curve for a sample containing risperidone generated with risperidone antibody 5_9 in the presence of a labeled risperidone competitive binding partner, with no dose response curve for aripiprazole, olanzapine, or quetiapine in the presence of a labeled competitive binding partner for each.

In FIG. 13, a sample containing risperidone is deposited in the sample zone and moves by capillary action through the conjugate zone (this time containing labeled aripiprazole, labeled olanzapine, labeled quetiapine, and labeled risperidone) and to the reaction zone. The reaction zone again contains risperidone antibody (5-9) in reaction zone 8. A typical dose response curve was generated as is shown in FIG. 13 only for risperidone, and not for aripiprazole, olanzapine, or quetiapine.

Figure 14:
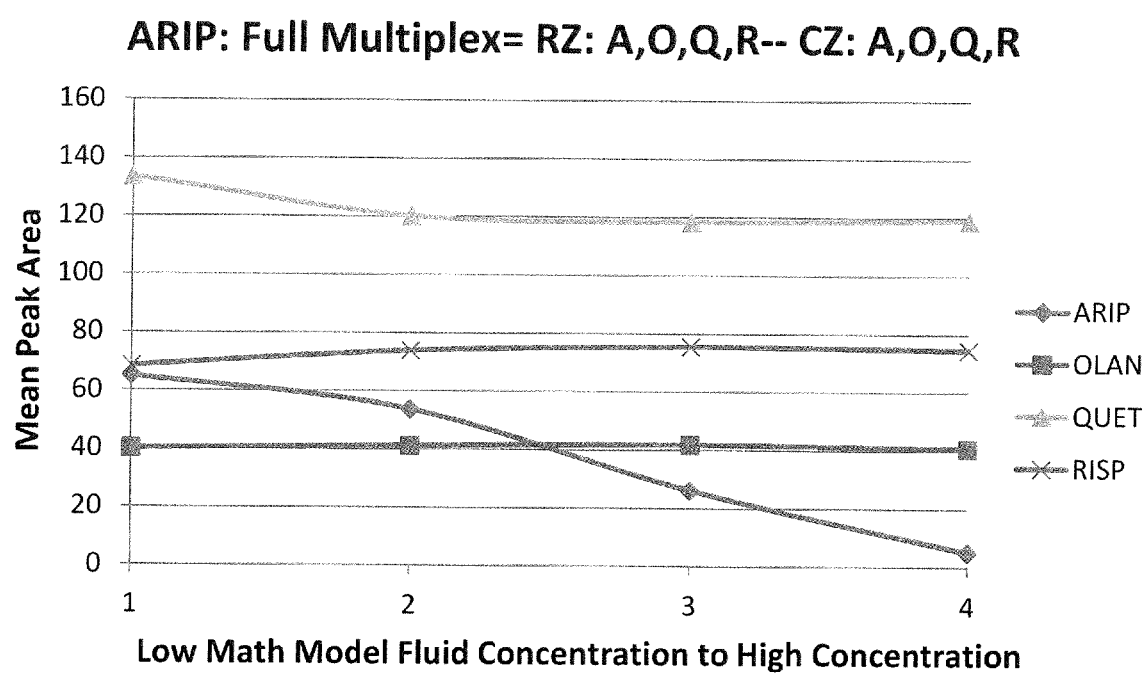
FIG. 14 shows a typical dose response curve for a sample containing aripiprazole generated with aripiprazole antibody 5C7 in the presence of a labeled aripiprazole competitive binding partner, with no dose response curve for olanzapine, quetiapine, or risperidone in the presence of antibody and labeled competitive binding partner for each.
Figure 15:
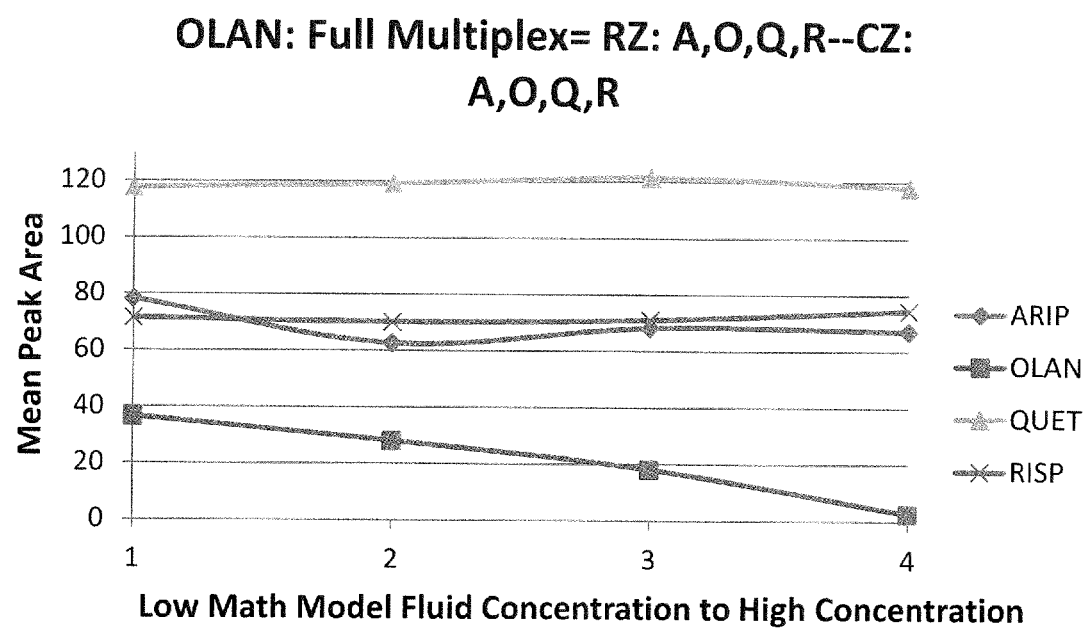
FIG. 15 shows a typical dose response curve for a sample containing olanzapine generated with olanzapine antibody 4G9-1 in the presence of a labeled olanzapine competitive binding partner, with no dose response curve for aripiprazole, quetiapine, or risperidone in the presence of antibody and labeled competitive binding partner for each.
Figure 16:
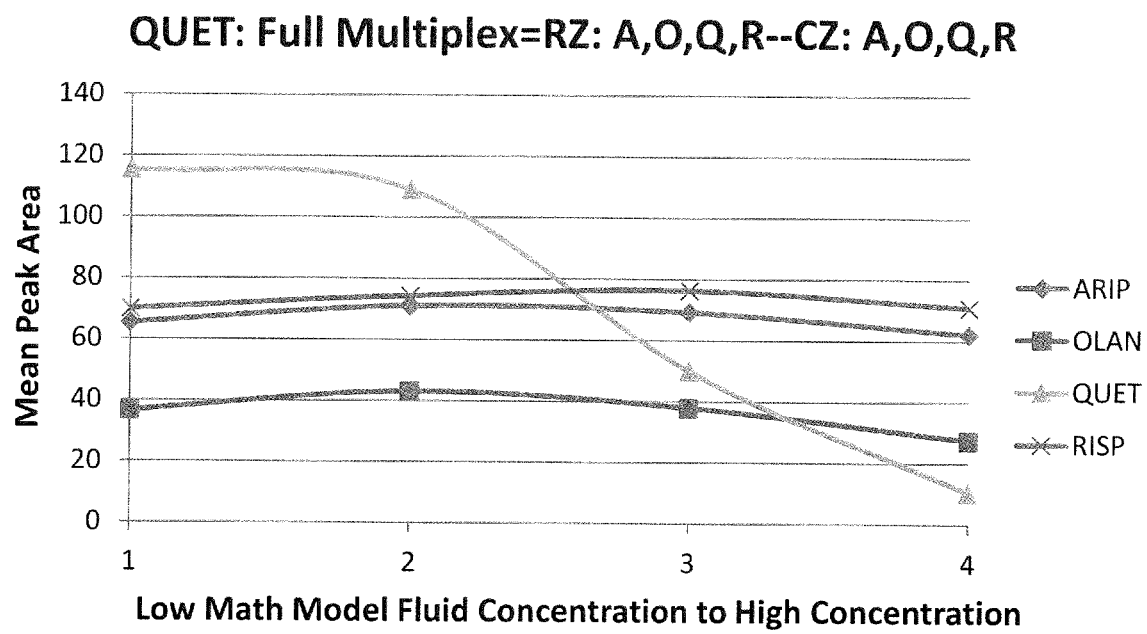
FIG. 16 shows a typical dose response curve for a sample containing quetiapine generated with quetiapine antibody 11 in the presence of labeled quetiapine competitive binding partner, with no dose response curve for aripiprazole, olanzapine, or risperidone in the presence of antibody and labeled competitive binding partner for each.
Figure 17:
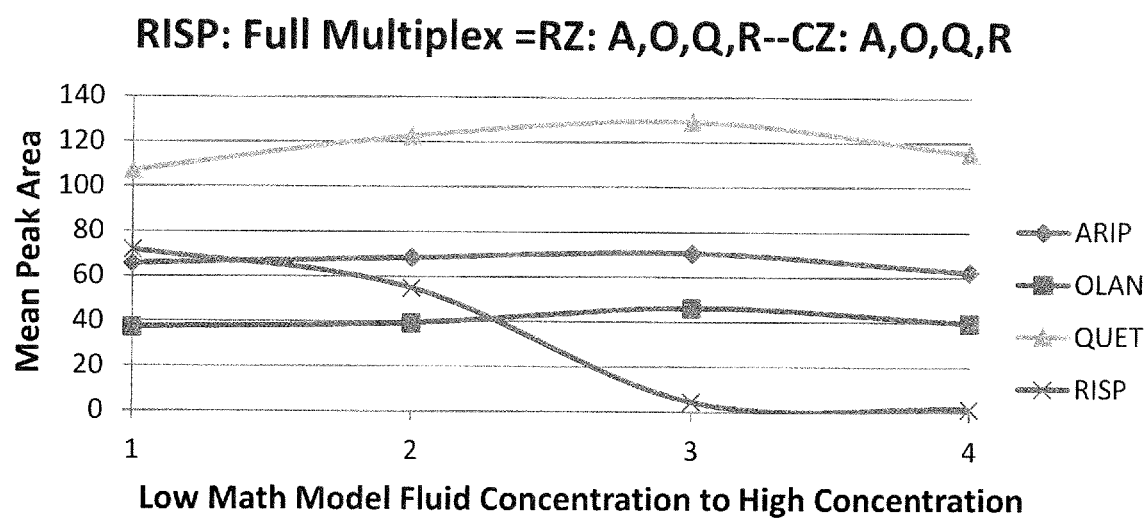
FIG. 17 shows a typical dose response curve for a sample containing risperidone generated with risperidone antibody 5_9 in the presence of a labeled risperidone competitive binding partner, with no dose response curve for aripiprazole, olanzapine, or quetiapine in the presence of antibody and labeled competitive binding partner for each.

FIGS. 14-17 show typical dose response curves for each assay in the presence of other conjugates and antibodies. In FIG. 14, a sample containing aripiprazole is deposited in the sample zone and moves by capillary action through the conjugate zone (again containing labeled aripiprazole, labeled olanzapine, labeled quetiapine, and labeled risperidone) and to the reaction zone. The reaction zone again contains aripiprazole antibody (5C7) in reaction zone 2, as well as olanzapine antibody (4G9-1) in reaction zone 4, quetiapine antibody (11) in reaction zone 6, and risperidone antibody (5-9) in reaction zone 8. A typical dose response curve was generated for aripiprazole, as is shown in FIG. 14. When a sample containing olanzapine was deposited in the sample zone of this chip, a typical dose response curve was generated for olanzapine as shown in FIG. 15. When a sample containing quetiapine was deposited in the sample zone of this chip, a typical dose response curve for quetiapine was generated as shown in FIG. 16. When a sample containing risperidone was deposited in the sample zone of this chip, a typical dose response curve for risperidone was generated as shown in FIG. 17.

Figure 18:
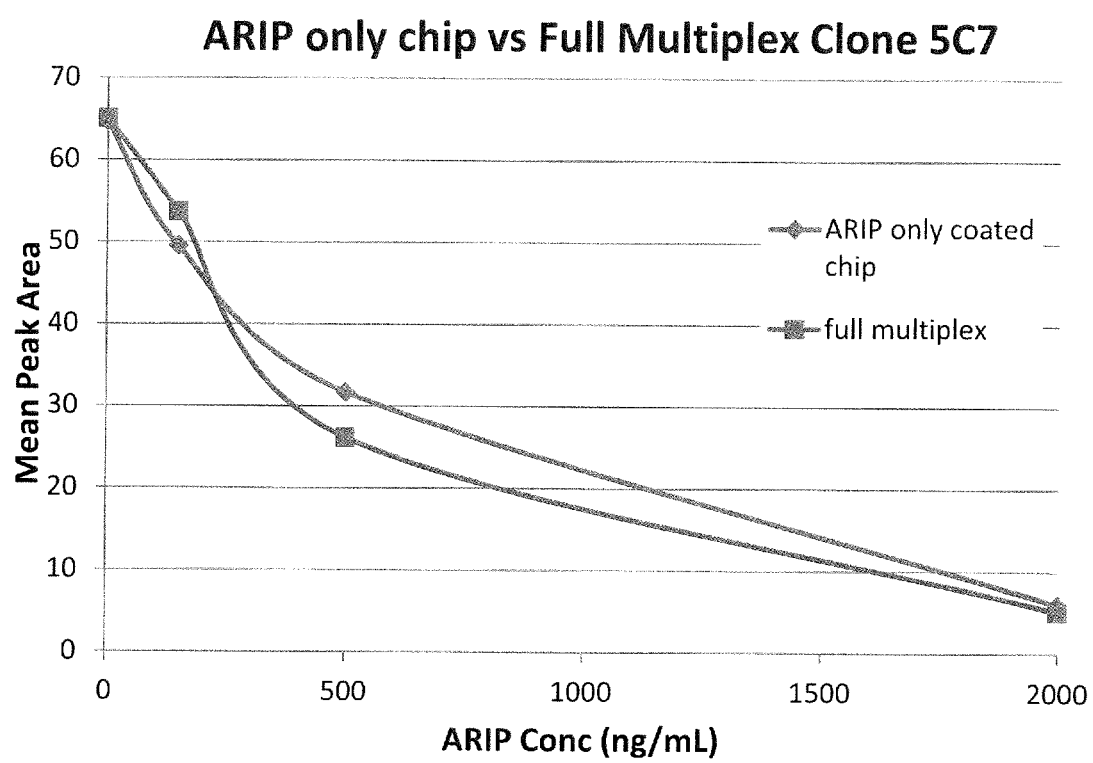
FIG. 18 shows a comparison of the aripiprazole dose response curve generated as a positive control to the aripiprazole dose response curve generated in the multiplex format.
Figure 19:
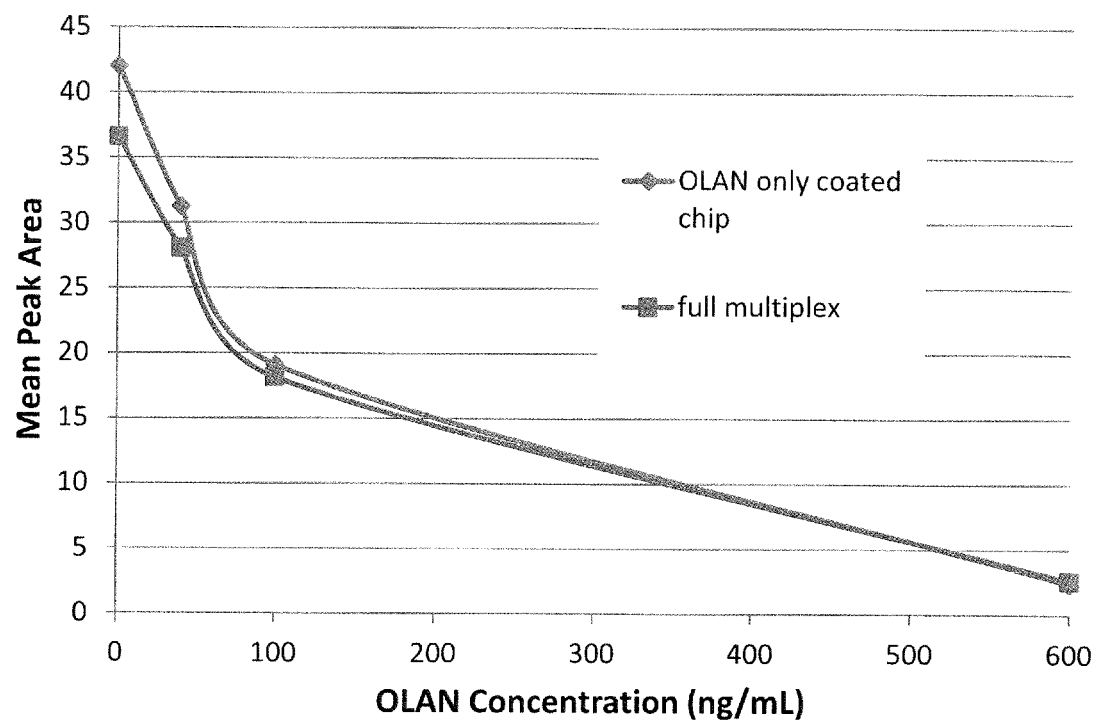
FIG. 19 shows a comparison of the olanzapine dose response curve generated as a positive control to the olanzapine dose response curve generated in the multiplex format.
Figure 20:
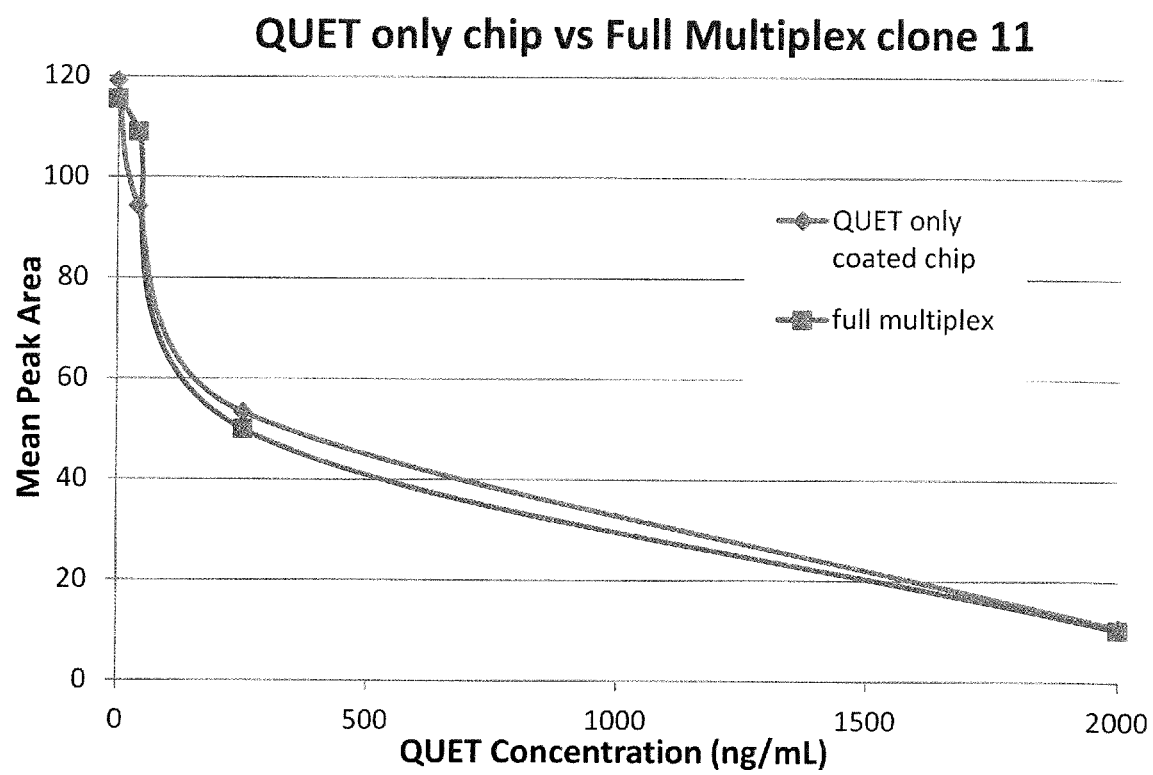
FIG. 20 shows a comparison of the quetiapine dose response curve generated as a positive control to the quetiapine dose response curve generated in the multiplex format.
Figure 21:
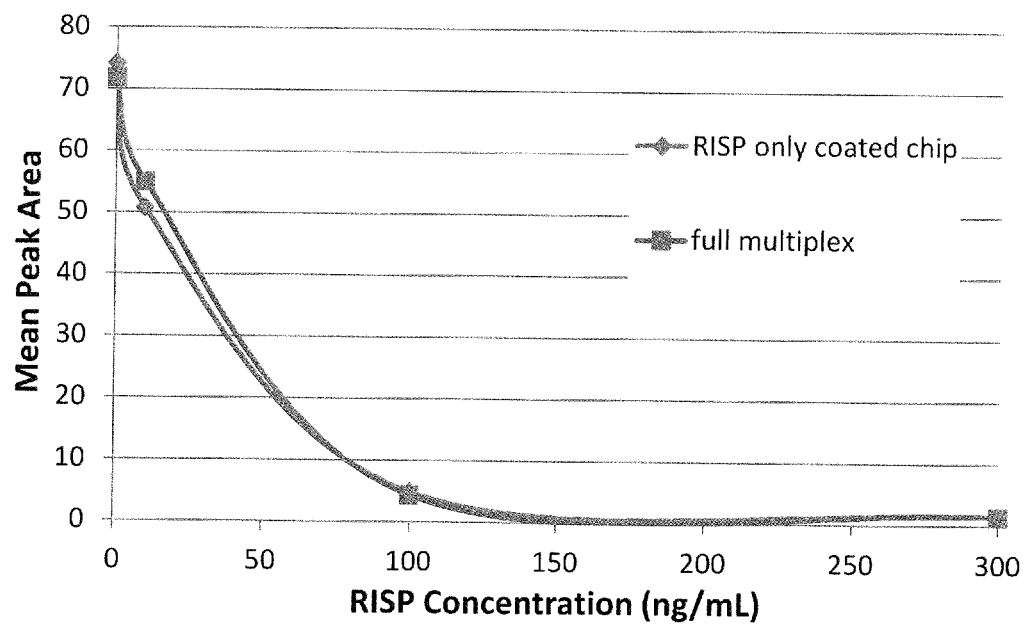
FIG. 21 shows a comparison of the risperidone dose response curve generated as a positive control to the risperidone dose response curve generated in the multiplex format.

FIGS. 18-21 show comparisons of dose response curves generated as positive controls (FIGS. 6-9) to dose response curves generated in the multiplex format (FIGS. 14-17). The comparison for aripiprazole is shown in FIG. 18; for olanzapine in FIG. 19; for quetiapine in FIG. 20; and for risperidone in FIG. 21. These figures show that the positive control curves are similar to the multiplex curves.

These data show that a lateral flow assay device of the subject invention can be used to detect multiple anti-psychotic drugs using a single sample from a patient on one portable, point-of-care device.

In describing the present invention and its various embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

What is claimed is:

1. An isolated antibody or a binding fragment thereof, which specifically binds to quetiapine, the isolated antibody or the binding fragment thereof comprising:
   (a) a light chain complementarity determining region (CDR) 1 sequence comprising amino acid residues 43 to 58 of SEQ ID NO:3, a light chain CDR2 sequence comprising amino acid residues 74 to 80 of SEQ ID NO:3, a light chain CDR3 sequence comprising amino acid residues 113 to 121 of SEQ ID NO:3, a heavy chain CDR1 sequence comprising amino acid residues 50 to 54 of SEQ ID NO:4, a heavy chain CDR2 sequence comprising amino acid residues 69 to 84 of SEQ ID NO:4, and a heavy chain CDR3 sequence comprising amino acid residues 117 to 126 of SEQ ID NO:4;
   (b) a light chain CDR1 sequence comprising amino acid residues 43 to 58 of SEQ ID NO:8, a light chain CDR2 sequence comprising amino acid residues 74 to 80 of SEQ ID NO:8, a light chain CDR3 sequence comprising amino acid residues 113 to 121 of SEQ ID NO:8, a heavy chain CDR1 sequence comprising amino acid residues 45 to 54 of SEQ ID NO:10, a heavy chain CDR2 sequence comprising amino acid residues 69 to 84 of SEQ ID NO:10, and a heavy chain CDR3 sequence comprising amino acid residues 117 to 119 of SEQ ID NO:10;
   (c) a light chain CDR1 sequence comprising amino acid residues 46 to 56 of SEQ ID NO:9, a light chain CDR2 sequence comprising amino acid residues 72 to 78 of SEQ ID NO:9, a light chain CDR3 sequence comprising amino acid residues 111 to 119 of SEQ ID NO:9, a heavy chain CDR1 sequence comprising amino acid residues 49 to 54 of SEQ ID NO:10, a heavy chain CDR2 sequence comprising amino acid residues 69 to 84 of SEQ ID NO:10, and a heavy chain CDR3 sequence comprising amino acid residues 117 to 119 of SEQ ID NO:10; or
   (d) a light chain CDR1 sequence comprising amino acid residues 46 to 55 of SEQ ID NO:17, a light chain CDR2 sequence comprising amino acid residues 71 to 77 of SEQ ID NO:17, a light chain CDR3 sequence comprising amino acid residues 110 to 118 of SEQ ID NO:17, a heavy chain CDR1 sequence comprising amino acid residues 50 to 54 of SEQ ID NO:18, a heavy chain CDR2 sequence comprising amino acid residues 69 to 85 of SEQ ID NO:18, and a heavy chain CDR3 sequence comprising amino acid residues 118 to 128 of SEQ ID NO:18.

2. The antibody or the binding fragment thereof of claim 1, wherein the antibody or the binding fragment thereof comprises a light chain CDR1 sequence comprising amino acid residues 43 to 58 of SEQ ID NO:3, a light chain CDR2 sequence comprising amino acid residues 74 to 80 of SEQ ID NO:3, a light chain CDR3 sequence comprising amino acid residues 113 to 121 of SEQ ID NO:3, a heavy chain CDR1 sequence comprising amino acid residues 50 to 54 of SEQ ID NO:4, a heavy chain CDR2 sequence comprising amino acid residues 69 to 84 of SEQ ID NO:4, and a heavy chain CDR3 sequence comprising amino acid residues 117 to 126 of SEQ ID NO:4.

3. The antibody or the binding fragment thereof of claim 1, wherein the antibody or the binding fragment thereof comprises a light chain CDR1 sequence comprising amino acid residues 43 to 58 of SEQ ID NO:8, a light chain CDR2 sequence comprising amino acid residues 74 to 80 of SEQ ID NO:8, a light chain CDR3 sequence comprising amino acid residues 113 to 121 of SEQ ID NO:8, a heavy chain CDR1 sequence comprising amino acid residues 45 to 54 of SEQ ID NO:10, a heavy chain CDR2 sequence comprising amino acid residues 69 to 84 of SEQ ID NO:10, and a heavy chain CDR3 sequence comprising amino acid residues 117 to 119 of SEQ ID NO:10.

4. The antibody or the binding fragment thereof of claim 1, wherein the antibody or the binding fragment thereof comprises a light chain CDR1 sequence comprising amino acid residues 46 to 56 of SEQ ID NO:9, a light chain CDR2 sequence comprising amino acid residues 72 to 78 of SEQ ID NO:9, a light chain CDR3 sequence comprising amino acid residues 111 to 119 of SEQ ID NO:9, a heavy chain CDR1 sequence comprising amino acid residues 49 to 54 of SEQ ID NO:10, a heavy chain CDR2 sequence comprising amino acid residues 69 to 84 of SEQ ID NO:10, and a heavy chain CDR3 sequence comprising amino acid residues 117 to 119 of SEQ ID NO:10.

5. The antibody or the binding fragment thereof of claim 1, wherein the antibody or the binding fragment thereof comprises a light chain CDR1 sequence comprising amino acid residues 46 to 55 of SEQ ID NO:17, a light chain CDR2 sequence comprising amino acid residues 71 to 77 of SEQ ID NO:17, a light chain CDR3 sequence comprising amino acid residues 110 to 118 of SEQ ID NO:17, a heavy chain CDR1 sequence comprising amino acid residues 50 to 54 of SEQ ID NO:18, a heavy chain CDR2 sequence comprising amino acid residues 69 to 85 of SEQ ID NO:18, and a heavy chain CDR3 sequence comprising amino acid residues 118 to 128 of SEQ ID NO:18.

6. The antibody or the binding fragment thereof of claim 1, wherein the binding fragment is selected from the group of fragments consisting of Fv, F(ab'), F(ab')2, seFv, minibody and diabody fragments.

7. The antibody of the binding fragment thereof of claim 1, wherein the antibody is a monoclonal antibody.

8. An assay kit comprising the antibody or the binding fragment thereof of claim 1.

9. An assay device comprising the antibody or the binding fragment thereof of claim 1.

10. The assay device of claim 9, wherein the device is a lateral flow assay device.

11. A method of detecting quetiapine in a sample comprising:
 (a) contacting a sample with the antibody or the binding fragment thereof of claim 1 labeled with a detectable marker, wherein the labeled antibody or the labeled binding fragment and quetiapine present in the sample form a labeled complex; and
 (b) detecting the labeled complex so as to detect quetiapine in the sample.

12. The method of claim 11, further comprising detecting the presence of one or more analytes in addition to quetiapine.

13. The method of claim 12, wherein the one or more analytes are anti-psychotic drugs other than quetiapine.

14. The method of claim 13, wherein the anti-psychotic drugs other than quetiapine are selected from the group consisting of: risperidone, paliperidone, aripiprazole, olanzapine, and metabolites thereof.

15. A competitive immunoassay method for detecting quetiapine in a sample comprising:
 (a) contacting a sample with the antibody or the binding fragment thereof of claim 1, and with quetiapine or a competitive binding partner of quetiapine, wherein one of the antibody or the binding fragment thereof and the quetiapine or the competitive binding partner thereof is labeled with a detectable marker, and wherein quetiapine in the sample competes with the quetiapine or competitive binding partner thereof for binding to the antibody or the binding fragment thereof; and
 (b) detecting the label so as to detect quetiapine in the sample.

16. The method of claim 15, wherein the quetiapine or competitive binding partner thereof is labeled with the detectable marker.

17. The method of claim 15, wherein the antibody or the binding fragment thereof is labeled with a detectable marker.

18. The method of claim 15, wherein the immunoassay is performed on a lateral flow assay device and the sample is applied to the device.

19. The method of claim 15, further comprising detecting the presence of one or more analytes in addition to quetiapine.

20. The method of claim 19, wherein the one or more analytes are anti-psychotic drugs other than quetiapine.

21. The method of claim 20, wherein the anti-psychotic drugs other than quetiapine are selected from the group consisting of: risperidone, paliperidone, aripiprazole, olanzapine, and metabolites thereof.

* * * * *

SEQUENCE LISTING

<160> NUMBER OF SEQ ID NOS: 18

<210> SEQ ID NO 1
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgaagttgc ctgttaggct gttggtgctg atgttctgga ttcctgcttc cagcagtggt      60
gttgtgttga cccaaactcc actctccctg cctgccagtc ttggagctca agcctccatc     120
tcttgcgcat ctagtcagag ccttctttac agtgatggaa acacctattt acattggtac     180
ctgcagaagc caggccagtc tccaaagctc ctgatctaca aagtttccag ccgaatttct     240
ggggtcccag acaggttcag tggcagtgga tcagggacag atttcactct cacgatcagc     300
agagtggagg ctgaggatct gggagtttat ttctgctctc aaagtacaca tgttccgtgg     360
acgttcggtg gaggcaccaa gctggaaatc aaa                                  393

<210> SEQ ID NO 2
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggctgtcc tggtgctgct cctctgcctg gtgacattcc caagctgtgt cctatcccag      60
gtgcagctga agcagtcagg acctggccta gtgcagccct cacagagcct gtccataacc     120
tgcacagtct cggattttc attaaggagt tatggtgtat attgggttcg ccagtctcca     180
ggaaagggtc tggagtggct gggagtgatt tggagaggtg aagcacaga ctacaatgca     240 gctttcatgt ccagactgag catctccaag gacaattcca agagacaagt tttatttaaa     300
atgaacagtc tgcaagatga tgacactgcc acctactatt gtgccatgat atttaaaagt     360
atggtagtgg gggatgtctg gggcacaggg accacggtca ccgtctcctc a             411

<210> SEQ ID NO 3
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Lys Leu Pro Val Arg Leu Leu Val Leu Met Phe Trp Ile Pro Ala
1               5                   10                  15

Ser Ser Ser Gly Val Val Leu Thr Gln Thr Pro Leu Ser Leu Pro Ala
                20                  25                  30

Ser Leu Gly Ala Gln Ala Ser Ile Ser Cys Ala Ser Gln Ser Leu
            35                  40                  45

Leu Tyr Ser Asp Gly Asn Thr Tyr Leu His Trp Tyr Leu Gln Lys Pro
        50                  55                  60

Gly Gln Ser Pro Lys Leu Leu Ile Tyr Lys Val Ser Ser Arg Ile Ser
65                  70                  75                  80

Gly Val Pro Asp Arg Phe Ser Gly Ser Gly Ser Gly Thr Asp Phe Thr
                85                  90                  95

Leu Thr Ile Ser Arg Val Glu Ala Glu Asp Leu Gly Val Tyr Phe Cys
            100                 105                 110

Ser Gln Ser Thr His Val Pro Trp Thr Phe Gly Gly Gly Thr Lys Leu
            115                 120                 125

Glu Ile Lys
        130

<210> SEQ ID NO 4
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Val Leu Val Leu Leu Cys Leu Val Thr Phe Pro Ser Cys
1               5                   10                  15

Val Leu Ser Gln Val Gln Leu Lys Gln Ser Gly Pro Gly Leu Val Gln
                20                  25                  30

Pro Ser Gln Ser Leu Ser Ile Thr Cys Thr Val Ser Asp Phe Ser Leu
            35                  40                  45

Arg Ser Tyr Gly Val Tyr Trp Val Arg Gln Ser Pro Gly Lys Gly Leu
        50                  55                  60

Glu Trp Leu Gly Val Ile Trp Arg Gly Gly Ser Thr Asp Tyr Asn Ala
65                  70                  75                  80

Ala Phe Met Ser Arg Leu Ser Ile Ser Lys Asp Asn Ser Lys Arg Gln
                85                  90                  95

Val Leu Phe Lys Met Asn Ser Leu Gln Asp Asp Thr Ala Thr Tyr
            100                 105                 110

Tyr Cys Ala Met Ile Phe Lys Ser Met Val Val Gly Asp Val Trp Gly
            115                 120                 125

Thr Gly Thr Thr Val Thr Val Ser Ser
        130                 135

<210> SEQ ID NO 5
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgaagttgc ctgttaggct gttggtgctg atgttctgga ttcctgcttc cagcagtgat        60
```

```
gttgtgctga cccagactcc actctccctg cctgtcagtc ttggagatca agcctccatc    120
tcttgcagat ctagtcagag ccttctttac agtaatggaa acacctattt acattggtac    180
ctgcagaagc caggccagtc tccaaagctc ctgatctaca aagtttccaa ccgattttct    240
ggggtcccag acaggttcag tggcagtgga tcagggacag atttcacact caagatcaac    300
agagtggagg ctgcggatct gggagtttat ttctgctctc aaagtacaca tgttccgtgg    360
acgttcggtg gaggcaccaa gctggaaatc aaa                                393
```

<210> SEQ ID NO 6
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atggacatca gggctcctgc tcagtttctt ggcatcttgt tgctctggtt tccaggtgcc     60
agatgtgaca tccagatgat tcagtctcca tcgtccatgt ttgcctctct gggagacaga    120
gtcagtctct cttgtcgggc tagtcagggc attagaggta atttagactg gtatcagcag    180
aaaccaggtg aactattaa actcctgatc tactccacat ccaatttaaa ttctggtgtc    240
ccatcaaggt tcagtggcag tgggtctggg tcagattatt ctctcaccat cagcagccta    300
gagtctgaag attttgcaga ctattactgt ctacagcgta atgcgtatcc gctcacgttc    360
ggtgctggga ccaagctgga gctgaaa                                        387
```

<210> SEQ ID NO 7
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
atgaaagtgt tgagtctgtt gtacctgttg acagccattc ctggtatcct gtctgatgta     60
cagcttcggg agtcaggacc tggcctcgtg aaaccttctc agtctctgtc tctcacctgc    120
tctgtcactg gcgactccat caccggtggt tattactgga actgggtccg gcagtttcca    180
ggaaacaaac tggaatggat gggctacata aactacgatg taccattca ctacaaccca    240 tctctcaaaa atcggatctc catcactcgt gacacatctc agaaccagtt tctcctgaag    300
ttgaattctg tgactgctga ggacacagcc acatattact gtgcaacctg ggactactgg    360
ggccaaggca ccactctcac agtctcctca                                     390
```

<210> SEQ ID NO 8
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Lys Leu Pro Val Arg Leu Leu Val Leu Met Phe Trp Ile Pro Ala
1               5                   10                  15

Ser Ser Ser Asp Val Val Leu Thr Gln Thr Pro Leu Ser Leu Pro Val
            20                  25                  30
```

Ser Leu Gly Asp Gln Ala Ser Ile Ser Cys Arg Ser Ser Gln Ser Leu
            35                  40                  45

Leu Tyr Ser Asn Gly Asn Thr Tyr Leu His Trp Tyr Leu Gln Lys Pro
 50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Asn Arg Val Glu Ala Ala Asp Leu Gly Val Tyr Phe Cys
            100                 105                 110

Ser Gln Ser Thr His Val Pro Trp Thr Phe Gly Gly Gly Thr Lys Leu
            115                 120                 125

Glu Ile Lys
            130

<210> SEQ ID NO 9
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Ile Arg Ala Pro Ala Gln Phe Leu Gly Ile Leu Leu Leu Trp
1               5                   10                  15

Phe Pro Gly Ala Arg Cys Asp Ile Gln Met Ile Gln Ser Pro Ser Ser
                20                  25                  30

Met Phe Ala Ser Leu Gly Asp Arg Val Ser Leu Ser Cys Arg Ala Ser
            35                  40                  45

Gln Gly Ile Arg Gly Asn Leu Asp Trp Tyr Gln Gln Lys Pro Gly Gly
         50                  55                  60

Thr Ile Lys Leu Leu Ile Tyr Ser Thr Ser Asn Leu Asn Ser Gly Val
65                  70                  75                  80

Pro Ser Arg Phe Ser Gly Ser Gly Ser Gly Ser Asp Tyr Ser Leu Thr
                85                  90                  95

Ile Ser Ser Leu Glu Ser Glu Asp Phe Ala Asp Tyr Tyr Cys Leu Gln
            100                 105                 110

Arg Asn Ala Tyr Pro Leu Thr Phe Gly Ala Gly Thr Lys Leu Glu Leu
            115                 120                 125

Lys

<210> SEQ ID NO 10
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Val Leu Ser Leu Leu Tyr Leu Leu Thr Ala Ile Pro Gly Ile
1               5                   10                  15

Leu Ser Asp Val Gln Leu Arg Glu Ser Gly Pro Gly Leu Val Lys Pro
                20                  25                  30

Ser Gln Ser Leu Ser Leu Thr Cys Ser Val Thr Gly Asp Ser Ile Thr
            35                  40                  45

Gly Gly Tyr Tyr Trp Asn Trp Val Arg Gln Phe Pro Gly Asn Lys Leu

```
            50                  55                  60
Glu Trp Met Gly Tyr Ile Asn Tyr Asp Gly Thr Ile His Tyr Asn Pro
 65                  70                  75                  80

Ser Leu Lys Asn Arg Ile Ser Ile Thr Arg Asp Thr Ser Gln Asn Gln
                 85                  90                  95

Phe Leu Leu Lys Leu Asn Ser Val Thr Ala Glu Asp Thr Ala Thr Tyr
             100                 105                 110

Tyr Cys Ala Thr Trp Asp Tyr Trp Gly Gln Gly Thr Thr Leu Thr Val
        115                 120                 125

Ser Ser
    130

<210> SEQ ID NO 11
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgaagttgc ctgttaggct gttggtgctg atgttctgga ttcctgcttc cagtagtgat      60
gttgtgatga cccaaactcc actctccctg cctgtcagtc ttggagatca agcctccatc     120
tcttgttggt ctagtcagag ccttgtagac agttatggaa acacctattt acattggtat     180
ctgcagaagc caggccagtc tccaaagctc ctgatctaca agtttccaa ccgattttct      240 ggggtcccag acaggttcag tggcagtgga tcagggacag atttcacact caagatcagc     300
agagtggagg ctgaggatct gggaatttac ttttgctctc aaactacata tgttccgtat     360
acgttcggat cggggaccaa gctggaaatg aaa                                   393

<210> SEQ ID NO 12
<211> LENGTH: 420
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggaatgga cctgggtctt tctcttcctc ctgtcagtaa ctgcaggtgt ccactcccag      60
gttcagctgc accagtctgg agctgagctg atgaagcctg gggcctcagt gaagatatcc     120
tgcaaggcta ccggctacac atttagtagg tactggataa gtggataaa acagaggcct      180 ggccatggcc ttgagtggat tggagagttt ctacctggaa gtggaaattc taactacaat     240
gctaaattca gggcaaggc caccttcact gcagcaacat cctccaacac agcctacatg      300
caactcagca gtgtgacatc tgaagactct gccgtctatt tctgtgcaac tggtacgat      360 gttaactacc gctatcttat ggactattgg ggtcaaggaa cctcagtcac cgtctcctca     420

<210> SEQ ID NO 13
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Lys Leu Pro Val Arg Leu Leu Val Leu Met Phe Trp Ile Pro Ala
```

```
                1               5                  10                 15
Ser Ser Ser Asp Val Val Met Thr Gln Thr Pro Leu Ser Leu Pro Val
                20                 25                 30

Ser Leu Gly Asp Gln Ala Ser Ile Ser Cys Trp Ser Ser Gln Ser Leu
                35                 40                 45

Val Asp Ser Tyr Gly Asn Thr Tyr Leu His Trp Tyr Leu Gln Lys Pro
         50                 55                 60

Gly Gln Ser Pro Lys Leu Leu Ile Tyr Lys Val Ser Asn Arg Phe Ser
 65              70                 75                 80

Gly Val Pro Asp Arg Phe Ser Gly Ser Gly Ser Gly Thr Asp Phe Thr
                    85                 90                 95

Leu Lys Ile Ser Arg Val Glu Ala Glu Asp Leu Gly Ile Tyr Phe Cys
                100                105                110

Ser Gln Thr Thr Tyr Val Pro Tyr Thr Phe Gly Ser Gly Thr Lys Leu
                115                120                125

Glu Met Lys
    130

<210> SEQ ID NO 14
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Glu Trp Thr Trp Val Phe Leu Phe Leu Leu Ser Val Thr Ala Gly
 1               5                  10                 15

Val His Ser Gln Val Gln Leu His Gln Ser Gly Ala Glu Leu Met Lys
                20                 25                 30

Pro Gly Ala Ser Val Lys Ile Ser Cys Lys Ala Thr Gly Tyr Thr Phe
                35                 40                 45

Ser Arg Tyr Trp Ile Glu Trp Ile Lys Gln Arg Pro Gly His Gly Leu
        50                 55                 60

Glu Trp Ile Gly Glu Phe Leu Pro Gly Ser Gly Asn Ser Asn Tyr Asn
65                  70                 75                 80

Ala Lys Phe Lys Gly Lys Ala Thr Phe Thr Ala Thr Ser Ser Asn
                85                 90                 95

Thr Ala Tyr Met Gln Leu Ser Ser Val Thr Ser Glu Asp Ser Ala Val
                100                105                110

Tyr Phe Cys Ala Thr Trp Tyr Asp Val Asn Tyr Arg Tyr Leu Met Asp
                115                120                125

Tyr Trp Gly Gln Gly Thr Ser Val Thr Val Ser Ser
                130                135                140

<210> SEQ ID NO 15
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15 atggatttc aggtgcagat tttcagcttc ctgctaatca gtgcctcagt cataatgtcc      60
agaggagaaa atgtgctcac ccagtctcca gcaatcatgt ctgcaactct aggggagaag     120
```

```
gtcaccatga gctgcagggc cagctcaaat gtaaagtaca tgtactggta ccagcagagg    180
tcaggtgcct cccccaaact atggatttat tacacatcca acctggcttc tggagtccca    240
gctcgcttca gtggcagtgg gtctgggacc tcttattctc tcacaatcag cagcgtggag    300
gctgaagatg ctgccactta ttactgccag cagtttacta gttccccatt cacgttcggc    360
acggggacaa aattggaaat aaaa                                            384

<210> SEQ ID NO 16
<211> LENGTH: 417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atgggttggc tgtggaactt gctattcctg atggcagctg cccaaagtgc ccaagcacag    60
atccagttgg tacagtctgg acctgagctg aagaggcctg agagacagt caagatctcc    120 tgcaaggctt ctgggtatac cttcacaacc tatggaatga gctgggtgaa acaggctcca    180
ggaaagggtt taaagtggat gggctacata aactcctact ctggagtgcc aacatatgct    240
gatgacttca agggacggtt tgccttctct ttggagacct ctgccagcac tgcctatttg    300
cagatcaaca acctcaaata tgaggacacg gctacatatt tctgtgcaag aggcgagatc    360
tactctggtg actacgtgga ctactggggc caaggcacca ctctcacagt ctcctca      417

<210> SEQ ID NO 17
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asp Phe Gln Val Gln Ile Phe Ser Phe Leu Leu Ile Ser Ala Ser
1               5                   10                  15

Val Ile Met Ser Arg Gly Glu Asn Val Leu Thr Gln Ser Pro Ala Ile
            20                  25                  30

Met Ser Ala Thr Leu Gly Glu Lys Val Thr Met Ser Cys Arg Ala Ser
        35                  40                  45

Ser Asn Val Lys Tyr Met Tyr Trp Tyr Gln Gln Arg Ser Gly Ala Ser
    50                  55                  60

Pro Lys Leu Trp Ile Tyr Tyr Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Val Glu Ala Glu Asp Ala Ala Thr Tyr Tyr Cys Gln Gln Phe
            100                 105                 110

Thr Ser Ser Pro Phe Thr Phe Gly Thr Gly Thr Lys Leu Glu Ile Lys
        115                 120                 125

<210> SEQ ID NO 18
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 18

Met Gly Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Arg
            20                  25                  30

Pro Gly Glu Thr Val Lys Ile Ser Cys Lys Ala Ser Gly Tyr Thr Phe
            35                  40                  45

Thr Thr Tyr Gly Met Ser Trp Val Lys Gln Ala Pro Gly Lys Gly Leu
        50                  55                  60

Lys Trp Met Gly Tyr Ile Asn Ser Tyr Ser Gly Val Pro Thr Tyr Ala
65                      70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Tyr Glu Asp Thr Ala Thr
                100                 105                 110

Tyr Phe Cys Ala Arg Gly Glu Ile Tyr Ser Gly Asp Tyr Val Asp Tyr
            115                 120                 125

Trp Gly Gln Gly Thr Thr Leu Thr Val Ser Ser
            130                 135
```